US012662443B2

(12) United States Patent
Hakoda et al.

(10) Patent No.: US 12,662,443 B2
(45) Date of Patent: Jun. 23, 2026

(54) HIGH PURITY 4-HYDROXYSTYRENE SOLUTION, METHOD OF PRODUCING THE SAME, AND METHOD OF PRODUCING 4-HYDROXYSTYRENE POLYMER

(71) Applicant: MARUZEN PETROCHEMICAL CO., LTD., Tokyo (JP)

(72) Inventors: Yuma Hakoda, Ichihara (JP); Ryo Fujisawa, Ichihara (JP); Kazuhiko Haba, Ichihara (JP); Daisuke Tabata, Ichihara (JP); Yoshiyuki Furuya, Ichihara (JP); Ryo Sato, Ichihara (JP); Tomo Oikawa, Ichihara (JP)

(73) Assignee: Maruzen Petrochemical Co., Ltd., Tokyo (JP)

( * ) Notice: Subject to any disclaimer, the term of this patent is extended or adjusted under 35 U.S.C. 154(b) by 760 days.

(21) Appl. No.: 18/001,744

(22) PCT Filed: Jun. 18, 2021

(86) PCT No.: PCT/JP2021/023141

§ 371 (c)(1),
(2) Date: Dec. 14, 2022

(87) PCT Pub. No.: WO2021/256551

PCT Pub. Date: Dec. 23, 2021

(65) Prior Publication Data

US 2023/0242467 A1 Aug. 3, 2023

(30) Foreign Application Priority Data

Jun. 18, 2020 (JP) ................................ 2020-105613
Mar. 31, 2021 (JP) ................................ 2021-060761

(51) Int. Cl.
*C07C 37/56* (2006.01)
*C07C 39/20* (2006.01)
*C08F 12/22* (2006.01)

(52) U.S. Cl.
CPC ............. *C07C 37/56* (2013.01); *C08F 12/22* (2013.01)

(58) Field of Classification Search
CPC .......... C07C 37/56; C07C 39/20; C08F 12/22
See application file for complete search history.

(56) References Cited

U.S. PATENT DOCUMENTS

| | | | |
|---|---|---|---|
| 4,689,371 | A | 8/1987 | Elmore et al. |
| 4,898,916 | A | 2/1990 | Gupta |
| 5,087,772 | A | 2/1992 | Sheehan et al. |
| 5,861,231 | A | 1/1999 | Barclay et al. |
| 5,959,051 | A | 9/1999 | Kaneko et al. |

FOREIGN PATENT DOCUMENTS

| | | | |
|---|---|---|---|
| JP | S51-029137 | B1 | 8/1976 |
| JP | S63-023902 | A | 2/1988 |
| JP | H02-047109 | A | 2/1990 |
| JP | H04-283529 | A | 10/1992 |
| JP | H10-251315 | A | 9/1998 |
| JP | 2003-146923 | A | 5/2003 |
| JP | 2005-157401 | A | 6/2005 |
| JP | 2016-098181 | A | 5/2016 |
| JP | 2017-043543 | A | 3/2017 |
| TW | 194473 | B | 11/1992 |

OTHER PUBLICATIONS

Chinese Office Action (with English translation) dated Apr. 29, 2024 (Application No. 202180018744.4).
Korean Office Action (with English translation) dated May 22, 2025 (Application No. 10-2022-7029164).
English translation of the International Preliminary Report on Patentability (Chapter I) dated Dec. 29, 2022 (Application No. PCT/JP2021/023141).
4-Vinylphenol 10% solution in Propylene Glycol (online), retrieved Jul. 12, 2021at https://labchem-wako.fujifilm.com/jp/product/detail/W01FLC240601.html, Fujifilm Wako Pure Chemical Corporation (with English translation), 2 pp.
Taiwanese Office Action (Application No. 110122306) dated May 30, 2022 (with English translation).
International Search Report and Written Opinion (Application No. PCT/JP2021/023141) dated Jul. 27, 2021.
Chinese Office Action (with English translation) dated Jul. 9, 2024 (Application No. 202180018744.4).
Japanese Office Action (with English translation) dated Nov. 8, 2024 (Application No. 2022-531926).
Taiwanese Office Action (Application No. 110122306) dated Mar. 25, 2023 (with English translation) (17 pages).
Canadian Office Action dated Jul. 11, 2025 (Application No. 3,186,747).
Japanese Office Action (with English translation) dated Mar. 4, 2025 (Application No. 2022-531926).
Chinese Office Action (with English translation) dated Aug. 22, 2023 (Application No. 202180018744.4).
Korean Notice of Final Rejection (Application No. 10-2022-7029164) dated Jan. 23, 2026 (with English translation) (11 pages).

*Primary Examiner* — Sikarl A Witherspoon
(74) *Attorney, Agent, or Firm* — Muncy, Geissler, Olds & Lowe, P.C.

(57) ABSTRACT

Provided are a 4-hydroxystyrene solution with high purity and good storage stability that is suitable as a source for producing a 4-hydroxystyrene polymer on a commercial scale, and a method of producing the solution. The method of producing a 4-hydroxystyrene solution of the present invention includes the following steps (i) to (iv):(i) deprotection step for contacting 4-acetoxystyrene with a base in a solvent to produce 4-hydroxystyrene; (ii) neutralization step for adding an acid to the solution containing 4-hydroxystyrene after deprotection to neutralize the solution; (iii) step for washing the solution containing 4-hydroxystyrene after neutralization with water; and (iv) solvent replacement step for adding a solvent that can dissolve 4-hydroxystyrene to the solution containing 4-hydroxystyrene followed by distillation at 40° C. or lower to remove other components than 4-hydroxystyrene and excess solvent.

20 Claims, No Drawings

HIGH PURITY 4-HYDROXYSTYRENE SOLUTION, METHOD OF PRODUCING THE SAME, AND METHOD OF PRODUCING 4-HYDROXYSTYRENE POLYMER

BACKGROUND OF THE INVENTION

Field of the Invention

The present invention relates to 4-hydroxystyrene solutions with good storage stability and high purity, and methods of producing the same. The present invention also relates to methods of producing a 4-hydroxystyrene polymer, comprising polymerization using the 4-hydroxystyrene solution as a source.

Background Art

Polymers having a structural unit derived from 4-hydroxystyrene (hereinafter, referred to as "4-hydroxystyrene polymers") are used in many products such as photoresists, printed wiring boards, adhesives, PS printing plates, metal surface treating agents, and sealants. Especially in use for photoresists, there is a demand to highly reduce impurities contained in the polymers, such as insoluble component and metals, with the progress to finer pattern. To fill the need for further finer pattern rules, such as in EUV lithography and electron beam lithography, much stringent management of the properties of resist polymers will be required.

For production of 4-hydroxystyrene polymer, methods using 4-hydroxystyrene as a starting material, and methods using a monomer obtained by replacing the hydroxyl group in 4-hydroxystyrene with a protecting group are known.

Known methods using a monomer obtained by replacing the hydroxyl group in 4-hydroxystyrene with a protecting group are, for example, those comprising polymerizing 4-acetoxystyrene as a source material, and removing the protecting group by an action of an acid, base, or the like to expose a hydroxy group (Patent Literature 1 and 2). The methods allow for commercially stable production of polymer because of easy availability of high-purity acetoxystyrene. However, the method requires a deprotection reaction with an acid or base after polymerization, a subsequent neutralization reaction, or the like, which results in a demerit of increasing the number of manufacturing steps and proportionately increasing the manufacturing cost. In addition, increase in the number of steps may proportionately increases the risk of contamination with impurities. In the case of a polymer for use in chemically amplified photoresists, the polymer contains structural units having acid dissociable groups that dissociate by the action of acids, and thus some of the acid dissociable groups may have been eliminated during the deprotection reaction in acetoxystyrene units.

Methods using 4-hydroxystyrene as a starting material have also been studied (Patent Literature 3), but the purity of 4-hydroxystyrene has not been described at all. Furthermore, polymers have been produced only in a laboratory scale. This is because 4-hydroxystyrene is a very unstable compound and undergoes rapid polymerization forward even at room temperature, and thus is difficult to be produced and stored in large quantities as a source for industrial production of polymers.

A method for producing 4-hydroxystyrene with high purity has been known (Patent Literature 4), comprising reacting 4-acetoxystyrene with an alcohol in the presence of a catalytic amount of a suitable base.

In addition, a method for stably storing unstable 4-hydroxystyrene has been known (Patent Literature 5), comprising adding 3 to 1000 weight % of an alcohol, such as methanol, relative to 4-hydroxystyrene. However, it results in insufficient prevention of polymerization, and also essentially requires coexisting alcohol. For example, a polymerization material composition containing a 4-hydroxystyrene composition obtained by dehydrogenation of 4-ethylphenol, and methanol added thereto has also been disclosed (Patent Literature 6). However, the composition contains a large quantity of impurities such as catalyst residues and remaining ethylphenol from the 4-ethylphenol dehydrogenation, and thus the method is not suitable for production of resist resins for use in most advanced lithography.

Other methods for producing 4-hydroxystyrene at high yield and stably storing it have been disclosed (Patent Literature 7), comprising deprotecting a protected monomer of 4-hydroxystyrene in the presence of 1,3,5-trihydroxybenzene using a base catalyst, followed by crystallization to obtain a crystal of 4-hydroxystyrene; and comprising adding 0.01 mass % or more and 10 mass % or less of 1,3,5-trihydroxybenzene to 4-hydroxystyrene before storing. However, the polymer is contaminated with 1,3,5-trihydroxybenzene as an impurity, and thus is not suitable for resists for use in most advanced lithography.

CITATION LIST

Patent Literature

Patent Literature 1: JP H02-047109 A
Patent Literature 2: JP S63-023902 A
Patent Literature 3: JP 2005-157401 A
Patent Literature 4: JP H4-283529 A
Patent Literature 5: JP S51-29137 A
Patent Literature 6: JP H10-251315 A
Patent Literature 7: JP 2016-098181 A

SUMMARY OF THE INVENTION

Technical Problem

The present invention provides a 4-hydroxystyrene solution with high purity and good storage stability that is suitable as a source for producing a 4-hydroxystyrene polymer on a commercial scale, and a method of producing the solution. The present invention also provides a production method capable of producing a 4-hydroxystyrene polymer suitable as a resist for the most advanced lithography by a simple process without the need for deprotection step and on a commercial scale.

Solution to Problem

In order to achieve the above objects, the present inventors have intensively studied to find that a 4-hydroxystyrene solution in which the concentration of 4-hydroxystyrene is from 10 to 70%, and the 4-hydroxystyrene polymer content relative to 4-hydroxystyrene is 0.5% or less, can prevent polymer production and be stably stored over a long period. For production of the 4-hydroxystyrene solution, the present inventors have further found that a 4-hydroxystyrene solution with high purity and good storage stability can be produced on a commercial scale by producing 4-hydroxystyrene in a deprotection reaction using 4-acetoxystyrene as a starting material and a base catalyst; neutralizing it; and adding a solvent that can dissolve 4-hydroxystyrene to the solution containing 4-hydroxystyrene followed by evaporation under reduced pressure at 40° C. or lower to remove other components than 4-hydroxystyrene and excess solvent for solvent replacement without crystallization of 4-hydroxystyrene. The present inventors have also found that a polymer having a structural unit derived from 4-hydroxystyrene with highly prevented contamination of insoluble components and metallic impurities can be produced by using the 4-hydroxystyrene solution for polymerization in a simple process without the need for deprotection step and on a commercial scale, thereby completing the present invention.

Accordingly, in accordance with the present invention, there are provided:

[1] A method of producing a 4-hydroxystyrene solution, comprising the following steps (i) to (iv):

(i) deprotection step for contacting 4-acetoxystyrene with a base in a solvent to produce 4-hydroxystyrene;

(ii) neutralization step for adding an acid to the solution containing 4-hydroxystyrene after deprotection to neutralize the solution;

(iii) step for washing the solution containing 4-hydroxystyrene after neutralization with water;

(iv) solvent replacement step for adding a solvent that can dissolve 4-hydroxystyrene to the solution containing 4-hydroxystyrene followed by distillation at 40° C. or lower to remove other components than 4-hydroxystyrene and excess solvent.

[2] The method of producing a 4-hydroxystyrene solution according to [1], wherein the base used in the deprotection step is subjected to bubbling with an inert gas to remove dissolved oxygen before use, and wherein the deprotection step is performed under a nitrogen atmosphere.

[3] The method of producing a 4-hydroxystyrene solution according to [1] or [2], wherein the acid used in the neutralization step is subjected to bubbling with an inert gas to remove dissolved oxygen before use.

[4] The method of producing a 4-hydroxystyrene solution according to any one of [1] to [3], wherein the base used in the deprotection step is a base selected from the group consisting of lithium hydroxide, sodium hydroxide, potassium hydroxide, sodium methoxide, potassium methoxide, sodium ethoxide, potassium tert-butoxide, trimethylamine, triethylamine, ethanolamine, diazabicycloundecene, diazabicyclononene, 1,5,7-triazabicyclo[4.4.0]dec-5-ene, 7-methyl-1,5,7-triazabicyclo[4.4.0]dec-5-ene, 1,1,3,3-tetramethylguanidine, and tetramethylammonium hydroxide.

[5] The method of producing a 4-hydroxystyrene solution according to any one of [1] to [4], wherein the organic solvent used in the solvent replacement step is any one organic solvent selected from the group consisting of alcohols, ketones, ethers, glycol ethers, glycol ether esters, and esters.

[6] The method of producing a 4-hydroxystyrene solution according to any one of [1] to [5], wherein the final concentration of 4-hydroxystyrene in the solvent replacement step is 10 to 70 mass %.

[7] The method of producing a 4-hydroxystyrene solution according to any one of [1] to [6], further comprising a step of allowing the 4-hydroxystyrene solution to pass through a filter with nominal pore size of 1 μm or less before and/or after the solvent replacement step.

[8] A 4-hydroxystyrene solution, in which the concentration of 4-hydroxystyrene is from 10 to 70 mass %, and the chromatogram area of 4-hydroxystyrene in a gel permeation chromatography analysis of the solution is 99.5% or more when the total chromatogram area of components other than the organic solvent is considered as 100.

[9] The 4-hydroxystyrene solution according to [8], wherein the chromatogram area of 4-hydroxystyrene polymer relative to the chromatogram area of 4-hydroxystyrene in a gel permeation chromatography analysis of the solution is 0.5% or less.

[10] The 4-hydroxystyrene solution according to [8] or [9], wherein the chromatogram area of 4-hydroxystyrene is 99.7% or more.

[11] The 4-hydroxystyrene solution according to [8] or [9], wherein the chromatogram area of 4-hydroxystyrene is 99.9% or more.

[12] The 4-hydroxystyrene solution according to any one of [8] to [11], wherein the organic solvent is any one organic solvent selected from the group consisting of alcohols, ketones, ethers, glycol ethers, glycol ether esters, and esters.

[13] The 4-hydroxystyrene solution according to any one of [8] to [12], which does not comprise a polymerization inhibitor.

[14] A polymerization material of a resist polymer, comprising the 4-hydroxystyrene solution according to any one of [8] to [13].

[15] A method of producing a polymer having a structural unit derived from 4-hydroxystyrene, comprising polymerization using the 4-hydroxystyrene solution according to any one of [8] to [13] as a polymerization material alone or in combination with anther monomer that can be copolymerized with the polymerization material.

[16] A method of producing a polymer having a structural unit derived from 4-hydroxystyrene, comprising polymerization of the 4-hydroxystyrene solution produced by the method according to any one of [1] to [7] as a polymerization material alone or in combination with anther monomer that can be copolymerized with the polymerization material.

[17] A method of producing a polymer having a structural unit derived from 4-hydroxystyrene, comprising:

a step of producing a 4-hydroxystyrene solution by the method according to any one of [1] to [7]; and a step of polymerization using the 4-hydroxystyrene solution produced in the above step as a polymerization material alone or in combination with another monomer that can be copolymerized with 4-hydroxystyrene.

[18] A method of producing a polymer according to any one of [15] to [17], wherein the another copolymerizable monomer include a monomer having an acid dissociable group.

[19] A method of producing a polymer according to [18], wherein the monomer having an acid dissociable group is a group having a tertiary carbon atom that attaches to an oxygen atom.

[20] A method of producing a polymer according to any one of [15] to [19], wherein the method is applied in polymerization using a polymerization tank with a volume of 30 L or more.

Advantageous Effects of Invention

In accordance with the present invention, a 4-hydroxystyrene solution with high purity and good storage stability can be produced simply and on a commercial scale. Furthermore, a 4-hydroxystyrene polymer suitable as a resist for the most advanced lithography can be produced by a simple process without the need for deprotection step and on a commercial scale.

DETAILED DESCRIPTION OF THE INVENTION

The method of producing a 4-hydroxystyrene solution, the 4-hydroxystyrene solution, and the method of producing a 4-hydroxystyrene polymer of the present invention will be described in detail below.

<Method of Producing 4-hydroxystyrene Solution>

(i) Deprotection Step

The deprotection step is a step for contacting 4-acetoxystyrene with a base in a solvent to eliminate the acetyl group and produce 4-hydroxystyrene.

The base used in the deprotection reaction is not particularly limited, and specific examples include alkali metal hydroxides such as lithium hydroxide, sodium hydroxide, and potassium hydroxide; alkali metal alkoxides such as sodium methoxide, potassium methoxide, sodium ethoxide, and potassium tert-butoxide; trimethylamine, triethylamine, ethanolamine, diazabicycloundecene, diazabicyclononene, 1,5,7-triazabicyclo[4.4.0]dec-5-ene, 7-methyl-1,5,7-triazabicyclo[4.4.0]dec-5-ene, 1,1,3,3-tetramethylguanidine, and tetramethylammonium hydroxide. Especially, sodium hydroxide, potassium hydroxide, sodium methoxide, potassium methoxide, sodium ethoxide, potassium tert-butoxide, trimethylamine, triethylamine, diazabicycloundecene, diazabicyclononene, 1,5,7-triazabicyclo[4.4.0]dec-5-ene, 7-methyl-1,5,7-triazabicyclo[4.4.0]dec-5-ene, 1,1,3,3-tetramethylguanidine, and tetramethylammonium hydroxide are preferable, and sodium hydroxide, potassium hydroxide, sodium methoxide, potassium methoxide, diazabicycloundecene, diazabicyclononene, and tetramethylammonium hydroxide are more preferable. The bases described above may be used alone or in combination of two or more of them.

The amount of the base used is preferably from 0.1 molar equivalents to 10.0 molar equivalents relative to 4-acetoxystyrene, and more preferably from 0.5 molar equivalents to 3.0 molar equivalents. When the amount of the base used is within the range described above, a sufficient reaction rate is likely to be obtained.

Preferably, the base is supplied in a solution state to the reaction system. Further preferably, the base solution is previously subjected to bubbling with an inert gas such as a nitrogen gas. Use of a degassed base solution has an effect of preventing production of hydroxystyrene polymers during the deprotection reaction.

Preferably, the deprotection reaction is performed in an organic solvent. The organic solvent is not particularly limited as long as it can dissolve 4-acetoxystyrene. Specific examples include alcohols such as methanol, ethanol, n-propyl alcohol, isopropyl alcohol, n-butyl alcohol, sec-butyl alcohol, tert-butyl alcohol, isobutyl alcohol, n-amyl alcohol, isoamyl alcohol, n-hexyl alcohol, n-heptyl alcohol, n-octyl alcohol, n-nonyl alcohol, n-decyl alcohol, lauryl alcohol, cetyl alcohol, stearyl alcohol, benzyl alcohol, triphenylcarbinol, ethylene glycol, 1,2-propanediol, 1,3-propanediol, and 1,4-butanediol; ketones such as methyl ethyl ketone, diethyl ketone, methyl isobutyl ketone, and cyclohexanone; hydrocarbons such as pentane, hexane, heptane, octane, isooctane, decane, cyclopentane, cyclohexane, benzene, toluene, and xylene; ethers such as diethylene glycol dimethyl ether, diethylene glycol diethyl ether, triethylene glycol dimethyl ether, triethylene glycol diethyl ether, tetrahydrofuran, diethyl ether, diisopropyl ether, and methyl tert-butyl ether; and nitrile solvents such as acetonitrile and propionitrile. The organic solvents may be used alone or in combination of two or more of them. Among them, the alcohols are preferable, and especially methanol, ethanol, n-propyl alcohol, and isopropyl alcohol are preferable. Preferably, a solution of 4-acetoxystyrene dissolved in the organic solvent is previously subjected to bubbling with an inert gas such as a nitrogen gas. This has an effect of preventing production of hydroxystyrene polymers during the deprotection reaction.

The reaction temperature of the deprotection reaction is usually −20 to 50° C., preferably −10 to 20° C., and more preferably −5 to 10° C., from the viewpoint of preventing polymerization reaction.

The reaction time is not particularly limited as long as it is sufficient for 4-acetoxystyrene to completely convert into 4-hydroxystyrene. The completion of the reaction can be determined by analyzing the product in the reaction solution by $^{1}$H-NMR, gas chromatography, gel permeation chromatography, or other methods.

Preferably, the deprotection reaction of 4-acetoxystyrene is performed in an inert gas atmosphere such as nitrogen.

(ii) Neutralization Step

The neutralization step is a step for neutralizing the base catalyst remaining in the reaction solution after the deprotection reaction by addition of an acid. The type of the acid used for neutralization is not particularly limited, and specific examples include formic acid, hydrochloric acid, acetic acid, oxalic acid, sulfuric acid, trifluoroacetic acid, and methanesulfonic acid. Preferably, the acid used for neutralization is diluted with a solvent as necessarily, and subjected to bubbling with an inert gas such as a nitrogen gas in advance. This has an effect of preventing production of 4-hydroxystyrene polymers.

(iii) Washing Step

The washing step is a step for washing the solution containing 4-hydroxystyrene after neutralization with water. Preferably, the solution containing 4-hydroxystyrene is extracted with an organic solvent that can dissolve 4-hydroxystyrene and be separated from water, and washed with deionized water to remove byproducts, salts, and other impurities.

The solvent used for extraction of 4-hydroxystyrene preferably can dissolve 4-hydroxystyrene and be separated from water, and more preferably has the same boiling point as or a boiling point lower than that of the solvent used in the solvent replacement step described below. This enables easy evaporation and removal of the extraction solvent in the subsequent solvent replacement step, thereby preventing the extraction solvent from remaining in the final product.

Specific examples include ethers such as diisopropyl ether, di-tert-butyl ether, methyl tert-butyl ether, ethyl tert-butyl ether, and diethylene glycol dimethyl ether; ketones such as methyl ethyl ketone, diethyl ketone, and methyl isobutyl ketone; esters such as methyl acetate and ethyl acetate; and hydrocarbons such as pentane, hexane, heptane, cyclohexane, and methylcyclohexane. Ethers are preferable, and methyl tert-butyl ether is especially preferable. The extraction solvents may be used alone or in combination of two or more of them.

The temperature during extraction is preferably in a range from −20 to lower than 50° C., and more preferably from −10 to 30° C. from the viewpoint of prevention of polymerization reaction.

Preferably, water used for washing the obtained extract containing 4-hydroxystyrene is deionized water to avoid contamination of metal ions. The amount of water used and the number of washing are not particularly limited, and can be determined as appropriate considering, for example, the ease of operation, the extraction efficiency of metal ions and the like, and the amount of waste liquid.

The temperature during washing is preferably from 0° C. to 50° C., and more preferably from 0° C. to 30° C.

(iv) Solvent Replacement Step

The solvent replacement step is a step for replacement of the 4-hydroxystyrene-containing extract with a desired solvent. In other words, a replacement solvent that can dissolve 4-hydroxystyrene is added to the 4-hydroxystyrene-containing extract, followed by distillation to remove other components than 4-hydroxystyrene, such as reaction byproducts and the extraction solvent, and excess replacement solvent. Production of 4-hydroxystyrene polymers can be prevented by solvent replacement without crystallization and obtaining a 4-hydroxystyrene solution, rather than by crystallizing 4-hydroxystyrene by a conventional crystallization method and then allowing it to be dissolved in a solvent.

A replacement solvent may be added to the 4-hydroxystyrene-containing extract before or after the start of distillation. Preferably, an additional replacement solvent is further added as appropriate during distillation. When the concentration of the 4-hydroxystyrene in the 4-hydroxystyrene-containing extract, a replacement solvent is preferably added in advance before distillation to prevent polymerization of 4-hydroxystyrene.

The temperature during distillation is preferably 40° C. or lower, more preferably from 20 to 35° C., and still more preferably from 20 to 30° C., from the viewpoint of preventing polymerization of 4-hydroxystyrene.

The distillation may be performed under atmospheric pressure, but is preferably performed under reduced pressure. The pressure during distillation under reduced pressure is not particularly limited, and can be adjusted as appropriate so that components other than 4-hydroxystyrene, such as reaction byproducts and an extraction solvent, and excess replacement solvent can be evaporated and removed. The pressure during distillation under reduced pressure is, for example, from 1 to 100 kPa, and preferably from 1 to 30 kPa.

The type of the replacement solvent is not particularly limited as long as it can dissolve 4-hydroxystyrene. When the obtained 4-hydroxystyrene solution is directly used as a polymerization material for producing a polymer, the replacement solvent more preferably can be used as a polymerization solvent. Specific examples include alcohols such as methanol, ethanol, propanol, butanol, and octanol; ketones such as acetone, methyl ethyl ketone, methyl isobutyl ketone, methyl amyl ketone, and cyclohexanone; ethers such as ethyl tert-butyl ether, tetrahydrofuran, dioxane, 1,2-dimethoxyethane, and diethylene glycol dimethyl ether; glycol ethers such as ethylene glycol monomethyl ether, ethylene glycol monoethyl ether, propylene glycol monomethyl ether, and propylene glycol monoethyl ether; glycol ether esters such as ethylene glycol monomethyl ether acetate, ethylene glycol monoethyl ether acetate, propylene glycol monomethyl ether acetate, and propylene glycol monoethyl ether acetate; esters such as ethyl acetate and ethyl lactate; N,N-dimethyl formamide, and acetonitrile. The alcohols, ketones, ethers, ether alcohols, ether esters, and esters are preferable, and methanol, ethanol, propanol, butanol, octanol, methyl ethyl ketone, methyl isobutyl ketone, tetrahydrofuran, ethylene glycol monomethyl ether, ethylene glycol monoethyl ether, propylene glycol monomethyl ether, ethylene glycol monomethyl ether acetate, ethylene glycol monoethyl ether acetate, propylene glycol monomethyl ether acetate, ethyl acetate, and ethyl lactate are more preferable, methanol, ethanol, 2-propanol, 2-butanol, n-octanol, methyl ethyl ketone, methyl isobutyl ketone, tetrahydrofuran, propylene glycol monomethyl ether, and propylene glycol monomethyl ether acetate are particularly preferable.

The amount of the replacement solvent used is not particularly limited, and is an amount that enables sufficient removal of impurities other than 4-hydroxystyrene and is determined in consideration of cost.

(v) Filtration Through Filter

Preferably, the 4-hydroxystyrene solution is filtered through a microfilter to remove insolubles such as polymers that are slightly produced during the production process. Filtration through a filter may be performed before, after, or before and after the solvent replacement.

The forms of the filter that can be used include membrane filters, hollow fiber membrane filters, pleated membrane filters, and filters filled with filter materials, such as highly purified cellulose and diatomaceous earth. The materials of the membrane filters, hollow fiber membrane filters, and pleated membrane filters are preferably polyolefins such as polyethylene, ultra high density polyethylene, and polypropylene, fluorine resins such as PTFE, and nylons, and especially nylons are preferable. The filter may also comprise an ion exchange group, a cationic charge modifier that causes zeta potential in the filter, or the like. Preferably, the ion exchange group is a weak acid or weak basic group. In the case of a weak acid or weak basic ion exchange group, polymerization of 4-hydroxystyrene can be prevented.

The nominal pore size of the filter is preferably 1 μm or less, more preferably 0.2 μm or less, and still more preferably 0.05 μm or less. The lower limit of the nominal pore size of the filter is not particularly limited, and usually is 0.01 μm.

(vi) Storage of 4-hydroxystyrene Solution

The temperature at which the produced 4-hydroxystyrene solution is stored is preferably from −15° C. to 40° C., more preferably from −15° C. to 20° C., and still more preferably from −15° C. to 5° C. to prevent polymerization during storage.

<4-hydroxystyrene Solution>

The 4-hydroxystyrene solution of the present invention is obtained by dissolving a certain concentration of 4-hydroxystyrene in a solvent. The storage stability of 4-hydroxystyrene can be improved by adjusting the concentration of 4-hydroxystyrene. The method of producing the 4-hydroxystyrene solution is not particularly limited. A 4-hydroxystyrene solution obtained by a production method comprising the steps (i) to (iv) as described above can be used. Alternatively, the 4-hydroxystyrene solution may be obtained by a method comprising, instead of the (iv) solvent replacement step, obtaining high-purity 4-hydroxystyrene crystal by conventionally known crystallization and then dissolving it in a solvent. Particularly preferably, the 4-hydroxystyrene solution is obtained by a production method comprising the steps (i) to (iv) as described above because the purity of 4-hydroxystyrene can be increased.

The concentration of 4-hydroxystyrene in the 4-hydroxystyrene solution is preferably from 10 mass % to 70 mass %, more preferably from 15 mass % to 60 mass %, and still more preferably from 20 mass % to 50 mass %. The concentration of 4-hydroxystyrene in the 4-hydroxystyrene solution is preferably 10 mass % or more, because decrease in the polymerization efficiency when used as a polymerization material can be prevented. The concentration is preferably 70 mass % or less, because deposition of 4-hydroxystyrene can be prevented. When putting particular emphasis on the stability during long-term storage, the concentration is particularly preferably 50 mass % or less.

The chromatogram area of 4-hydroxystyrene, as determined by gel permeation chromatography of a 4-hydroxystyrene solution in which the concentration of 4-hydroxystyrene is from 10 to 70 mass % when the total chromatogram area of components other than the organic solvent is considered as 100, is preferably 99.5% or more, more preferably 99.7% or more, and still more preferably 99.9% or more.

The amount of 4-hydroxystyrene polymers in the 4-hydroxystyrene solution with a 4-hydroxystyrene concentration of from 10 to 70 mass % preferably 0.5% or less relative to 4-hydroxystyrene, more preferably 0.3% or less, and still more preferably 0.1% or less. When the amount of 4-hydroxystyrene polymers is the above-described value or less, sufficient prevention of the progress of the polymerization reaction during storage has been successfully achieved.

Preferably, the 4-hydroxystyrene solution does not comprise any polymerization inhibitor. This allows for avoiding the risk of contamination of a resist polymer with impurities derived from a polymerization inhibitor when producing the resist polymer for most advanced lithography using the 4-hydroxystyrene solution. Even without addition of any polymerization inhibitor, the progression of the polymerization reaction during storage can be prevented.

The solvent used in the 4-hydroxystyrene solution is not particularly limited as long as it can dissolve 4-hydroxystyrene. When the obtained 4-hydroxystyrene solution is directly used as a polymerization material for producing a polymer, the solvent more preferably can be used as a polymerization solvent. Specific examples include alcohols such as methanol, ethanol, propanol, butanol, and octanol; ketones such as acetone, methyl ethyl ketone, methyl isobutyl ketone, methyl amyl ketone, and cyclohexanone; ethers such as ethyl tert-butyl ether, tetrahydrofuran, dioxane, 1,2-dimethoxyethane, and diethylene glycol dimethyl ether; glycol ethers such as ethylene glycol monomethyl ether, ethylene glycol monoethyl ether, propylene glycol monomethyl ether, and propylene glycol monoethyl ether; glycol ether esters such as ethylene glycol monomethyl ether acetate, ethylene glycol monoethyl ether acetate, propylene glycol monomethyl ether acetate, and propylene glycol monoethyl ether acetate; esters such as ethyl acetate and ethyl lactate; N,N-dimethyl formamide, and acetonitrile. The alcohols, ketones, ethers, ether alcohols, ether esters, and esters are preferable, and methanol, ethanol, propanol, butanol, octanol, methyl ethyl ketone, methyl isobutyl ketone, tetrahydrofuran, ethylene glycol monomethyl ether, ethylene glycol monoethyl ether, propylene glycol monomethyl ether, ethylene glycol monomethyl ether acetate, ethylene glycol monoethyl ether acetate, propylene glycol monomethyl ether acetate, ethyl acetate, and ethyl lactate are more preferable, methanol, ethanol, 2-propanol, 2-butanol, n-octanol, methyl ethyl ketone, methyl isobutyl ketone, tetrahydrofuran, propylene glycol monomethyl ether, and propylene glycol monomethyl ether acetate are particularly preferable.

<Method of Producing Polymer Having Structural Unit Derived from 4-hydroxystyrene>

The method of producing a polymer having a structural unit derived from 4-hydroxystyrene of the present invention comprises a step of polymerization of 4-hydroxystyrene used as a polymerization material alone or in combination with other monomers that can be copolymerized therewith. For the polymerization material, the 4-hydroxystyrene solution obtained by the production method described in <Method of Producing 4-hydroxystyrene Solution> and the 4-hydroxystyrene solution described in <4-hydroxystyrene Solution> can be directly used as the polymerization material. When the 4-hydroxystyrene solution is directly subjected to the polymerization step, the organic solvent dissolving 4-hydroxystyrene can be directly used as the polymerization solvent.

(Other Monomer that can be Copolymerized)

The other monomers that can be copolymerized are not particularly limited as long as they can be polymerized with 4-hydroxystyrene. For resist applications, known monomers that are used in production of resist polymers can be used.

Resist polymers are polymers whose solubility in a developer is changed by the action of an acid, and has at least one or more repeating unit (A) with a structure in which an alkali-soluble group are protected by an acid-cleavable dissolution inhibiting group. The acid-cleavable dissolution inhibiting group refers to a group that prevents the copolymer from being dissolved in an alkali developer while being dissociated by the action of an acid to allow the copolymer to be dissolved in an alkali developer. A repeating unit (B) having a lactone ring structure, a repeating unit (C) having a hydroxy group, or other units may be included to improve the polymer-substrate contact. Further, as necessary, a repeating unit (D) having a structure that prevents dissolution in an alkali developer and is stable against the action of an acid (hereinafter may be referred to as "acid-stable dissolution inhibiting structure") or other repeating units may be included.

(Repeating Unit (A))

The repeating unit (A) is a repeating unit having a structure in which an alkali-soluble group, such as a carboxyl, phenolic hydroxy, or sulfonic group, is protected by an acid-cleavable dissolution inhibiting group that is dissociated by the action of an acid. Preferably, the repeating unit (A) is a repeating unit in which an OH group, such as in a carboxyl, phenolic hydroxy, or sulfonic group in a repeating unit derived from (meth)acrylic acid, hydroxystyrene, or the like is protected by an acid-cleavable dissolution inhibiting group.

The acid-cleavable dissolution inhibiting group may be a structure represented by the formula (a1) or (a2).

[Chem 1]

(a1)

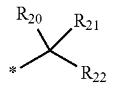

In the formula (a1), * represents a binding site of the formula (a1), and $R_{20}$ and $R_{21}$ each independently represent a $C_{1-4}$ hydrocarbon group, specifically including a $C_{1-4}$ alkyl group, such as a methyl, ethyl, n-propyl, i-propyl, n-butyl, or i-butyl group. $R_{22}$ represents a $C_{1-12}$ hydrocarbon group, specifically including a $C_{1-12}$ linear, branched, or cyclic alkyl group, such as a methyl, ethyl, n-propyl, i-propyl, n-butyl, i-butyl, cyclopentyl, cyclohexyl, norbornyl, tricyclo

[5.2.1.02,6]decanyl, adamantyl, or tetracyclo[4.4.0.12,5.17,10]dodecanyl group; or a $C_{6-12}$ aryl group, such as a phenyl or naphthyl group. Alternatively, $R_{22}$, together with $R_{20}$ or $R_{21}$, may form a ring, specifically a $C_{5-12}$ alicyclic ring, such as a cyclopentane ring, a cyclohexane ring, a norbornane ring, a tricyclo[5.2.1.02,6]decane ring, an adamantane ring, or a tetracyclo[4.4.0.12,5.17,10]dodecane ring. In particular, when $R_{22}$ contains, or $R_{22}$ and $R_{20}$ or $R_{21}$ join together to contain a saturated alicyclic ring, specifically including a cyclopentane ring, a cyclohexane ring, a norbornane ring, a tricyclo[5.2.1.02,6]decane ring, an adamantane ring, or a tetracyclo[4.4.0.12,5.17,10]dodecane ring, the difference in solubility in an alkali developer before and after lithography is large, which is desirable for drawing fine patterns.

[Chem 2]

(a2)

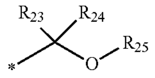

In the formula (a2), * represents a binding site of the formula (a2), and $R_{23}$ and $R_{24}$ each independently represent a hydrogen atom or a $C_{1-4}$ hydrocarbon group, specifically including a hydrogen atom, or a $C_{1-4}$ alkyl group, such as a methyl, ethyl, n-propyl, i-propyl, n-butyl, or i-butyl group. $R_{25}$ represents a $C_{1-12}$ hydrocarbon group, specifically including a $C_{1-12}$ linear, branched, or cyclic alkyl group, such as a methyl, ethyl, n-propyl, i-propyl, n-butyl, i-butyl, t-butyl, 2-ethylhexyl, cyclopentyl, cyclohexyl, norbornyl, tricyclo[5.2.1.02,6]decanyl, adamantyl, or tetracyclo[4.4.0.12,5.17,10]dodecanyl. Alternatively, $R_{23}$, together with $R_{24}$ or $R_{25}$, may form a ring. Specific examples of the ring in which $R_{23}$ and $R_{24}$ join together include a cyclopentane ring, a cyclohexane ring, a norbornane ring, a tricyclo[5.2.1.02,6]decane ring, an adamantine ring, and a tetracyclo[4.4.0.12,5.17,10]dodecane ring. Specific examples of the ring in which $R_{23}$ and $R_{25}$ join together include a hydrofuran ring and a hydropyran ring.

Specific examples of the repeating unit (A) will be described below, but the present invention is not limited thereto. One, or two or more having different structures may be selected from the repeating units (A) and used.

[Chem 3]

(A101)

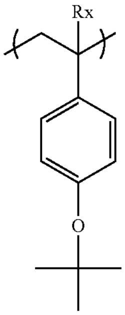

-continued (A102)

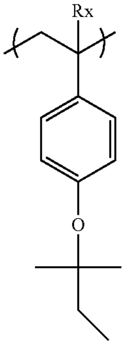

(A103)

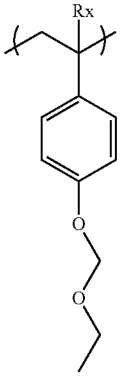

(A104)

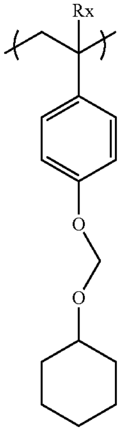

(A105)

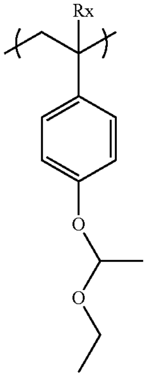

-continued
(A106)
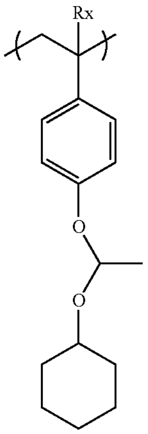
(A107)
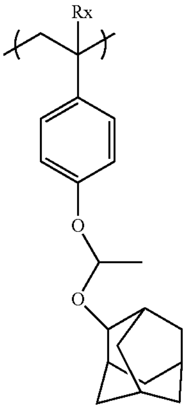
(A201)
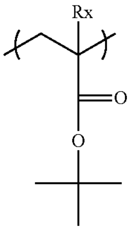
(A202)
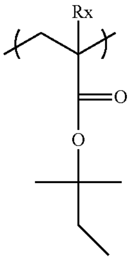
(A203)
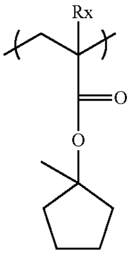
-continued
(A204)
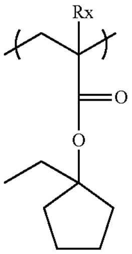
(A205)
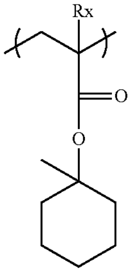
(A206)
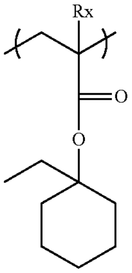
(A207)
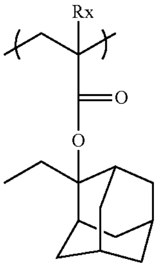
(A208)
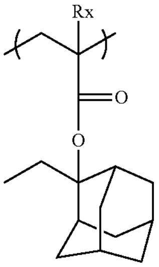
(A209)
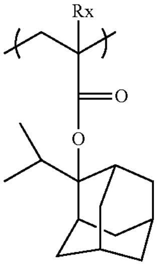

-continued
(A210)
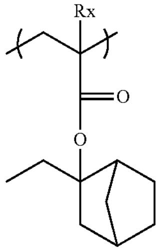
(A211)
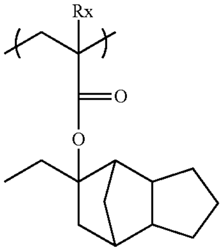
(A212)
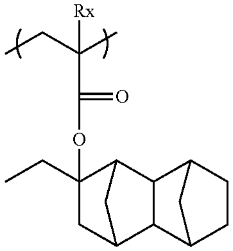
(A213)
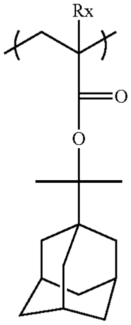
(A214)
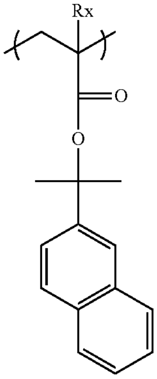
In the formulae, Rx represents H, $CH_3$, or $CF_3$.
[Chem 4]
(A301)
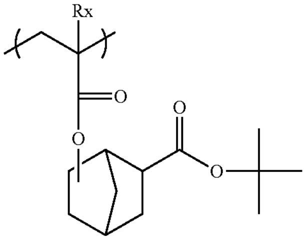
(A302)
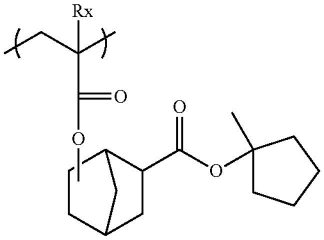
(A303)
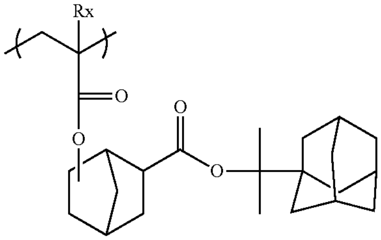
(A304)
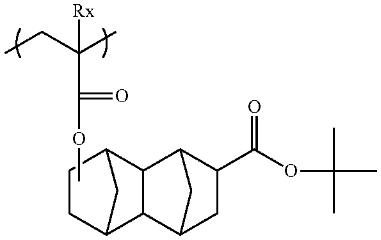
(A305)
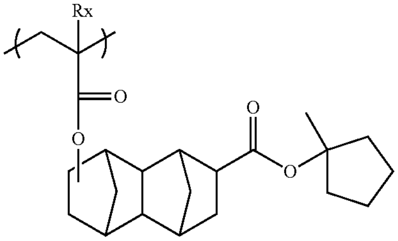
(A306)
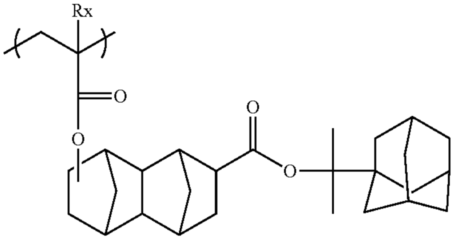

-continued
(A401)
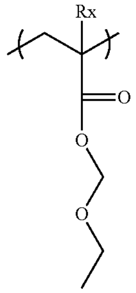
(A402)
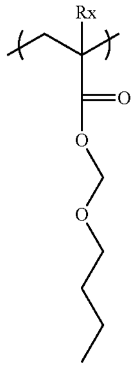
(A403)
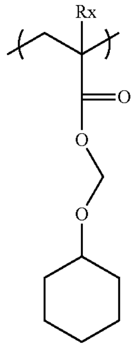
(A404)
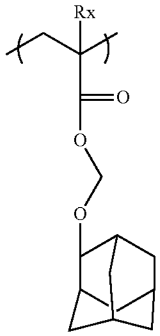
(A405)
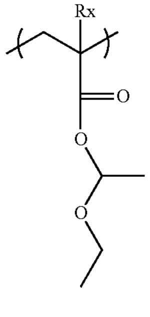
-continued
(A406)
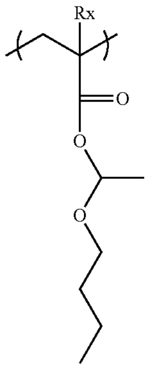
(A407)
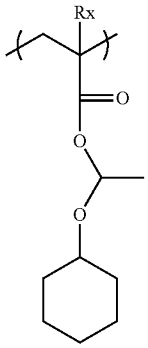
(A408)
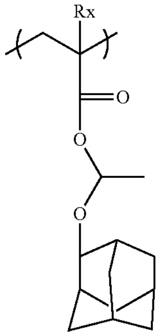
(A409)
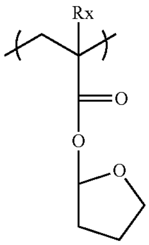
(A410)
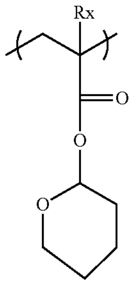

-continued (A411)

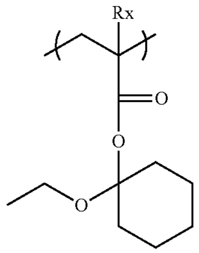

(A412)

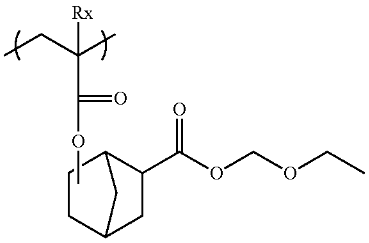

(A413)

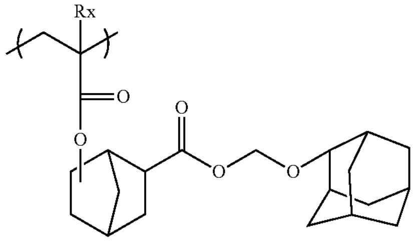

(A414)

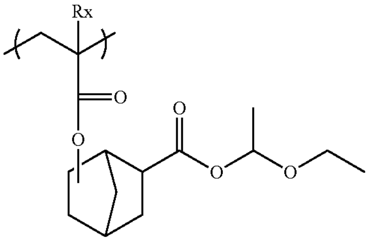

(A415)

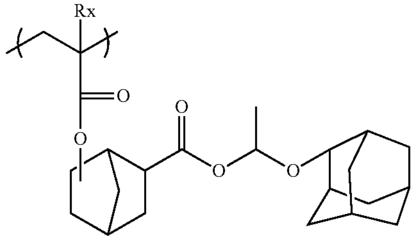

(A416)

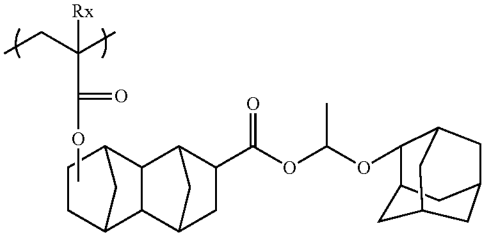

In the formulae, Rx represents H, $CH_3$, or $CF_3$.

(Repeating Unit (B))

The repeating unit (B) is a repeating unit having a lactone structure or sultone structure, and imparts functions to improve the adhesion to a substrate or an underlying film, and to control the solubility in a solvent for lithography or an alkali developer. Preferred examples include a structure represented by the formula (B1).

[Chem 5]

(B1)

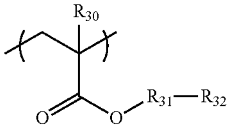

In the formula (B1), $R_{30}$ represents a hydrogen atom, or a $C_{1-4}$ hydrocarbon group that is optionally substituted with a fluorine atom, specifically including a hydrogen atom, or a $C_{1-4}$ alkyl groups, such as a methyl, ethyl, n-propyl, i-propyl, n-butyl, i-butyl, or trifluoromethyl group, and is preferably a hydrogen atom, a methyl group, or a trifluoromethyl group. $R_{31}$ represents a single bond or a divalent linking group. The divalent linking group represents a $C_{1-4}$ alkylene group, or the alkylene group substituted with an oxygen atom, carbonyl, or carbonyloxy group. $R_{32}$ represents a group containing a lactone structure represented by the formula (b).

[Chem 6]

(b)

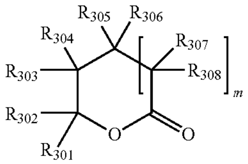

In the formula (b), any one of $R_{301}$ to $R_{308}$ represents a single bond that is a binding site of $R_{32}$, while the remaining of $R_{301}$ to $R_{308}$ each represent a hydrogen atom, a $C_{1-4}$ hydrocarbon group, or an alkoxy group. Alternatively, any one of $R_{301}$ to $R_{308}$ represents a $C_{3-14}$ hydrocarbon group that has a binding site of $R_{32}$, is combined with any one or two of the others of $R_{301}$ to $R_{308}$ to form a $C_{5-15}$ alicyclic ring, and optionally contains an oxygen atom or a sulfur atom, while any one or two of the remaining of $R_{301}$ to $R_{308}$ represent(s) a single bond(s) to form the $C_{5-15}$ alicyclic ring, and the others of $R_{301}$ to $R_{308}$ each represent a hydrogen atom, a $C_{1-4}$ hydrocarbon group, or an alkoxy group. m represents an integer of 0 or 1.

Specific examples of the alicyclic ring include a cyclopentane ring, a cyclohexane ring, a norbornane ring, a 7-oxa-norbornane ring, a 7-thia-norbornane ring, and tetracyclo[4.4.0.12,5.17,10]dodecane ring. Preferred examples include a norbornane ring, and a 7-oxa-norbornane ring. Specific examples of the $C_{1-4}$ hydrocarbon group include methyl, ethyl, n-propyl, i-propyl, n-butyl, and i-butyl groups. Specific examples of the $C_{1-4}$ alkoxy group include methoxy and ethoxy groups.

Particularly preferred examples of a lactone structure in which, in the formula (b), any one of $R_{301}$ to $R_{308}$ represents a single bond having the binding site of $R_{32}$, while the remaining of $R_{301}$ to $R_{308}$ each represent a hydrogen atom, a $C_{1-4}$ hydrocarbon group, or an alkoxy group, include a γ-butyrolactone structure and δ-valerolactone structure. Particularly preferred examples of a lactone structure in which any one of $R_{301}$ to $R_{308}$ represents a $C_{3-14}$ hydrocarbon group that has the binding site of $R_{32}$, is combined with any one or two of the others of $R_{301}$ to $R_{308}$ to form a $C_{5-15}$ alicyclic ring, and optionally contains an oxygen atom or a sulfur atom, while the others of $R_{301}$ to $R_{308}$ each represent a hydrogen atom, a $C_{1-4}$ hydrocarbon group, or an alkoxy group, include a 1,3-cyclohexanecarbolactone structure, a 2,6-norbornanecarbolactone structure, a 7-oxa-2,6-norbornanecarbolactone structure, and a 4-oxa-tricyclo[5.2.1.02,6]decane-3-one structure.

Specific examples of the repeating unit (B) will be described below, but the present invention is not limited thereto. One, or two or more having different structures may be selected from the repeating units (B) and used.

[Chem 7]

(B101)

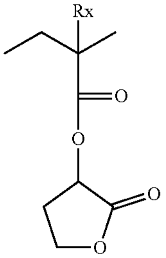

(B102)

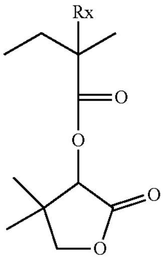

(B103)

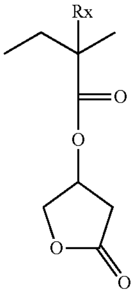

(B104)

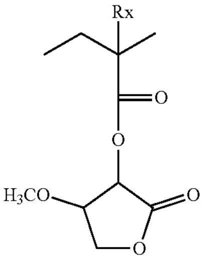

-continued (B105)

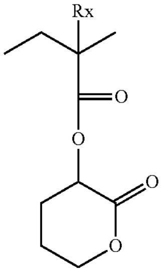

(B106)

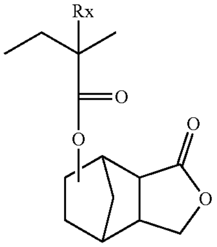

(B107)

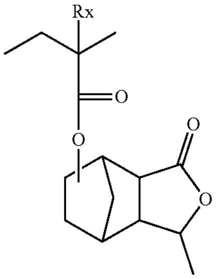

(B108)

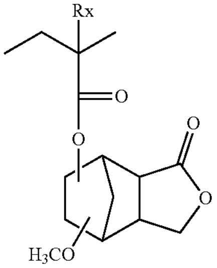

(B109)

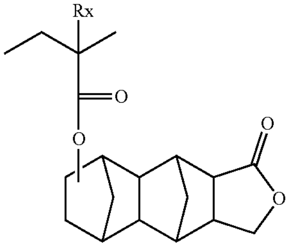

(B110)

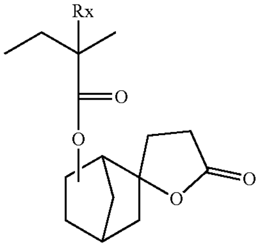

-continued
(B111)
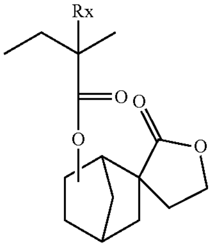
(B112)
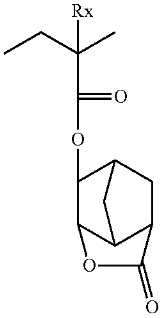
(B113)
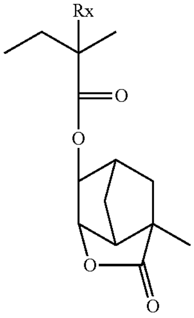
(B114)
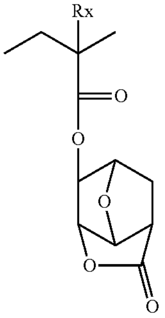
(B115)
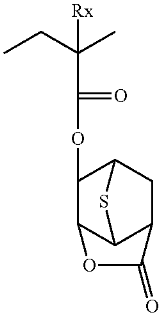
-continued
(B116)
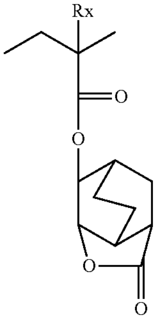
(B117)
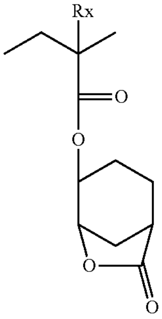
(B118)
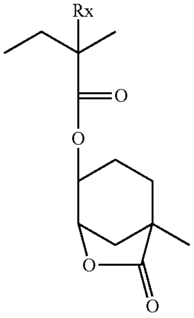
(B119)
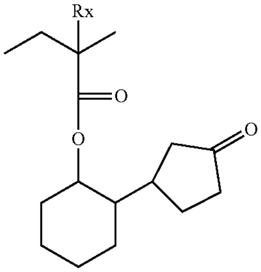
(B201)
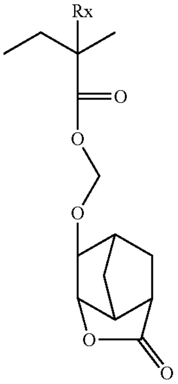

-continued (B202)

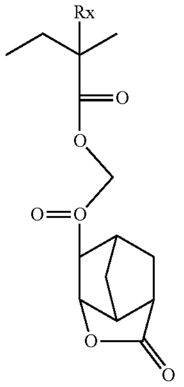

(B301)

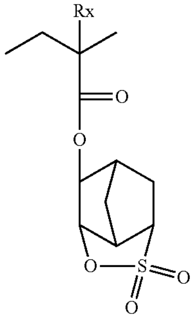

(B302)

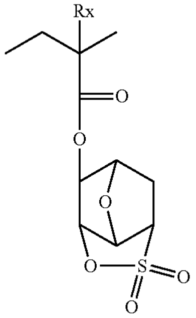

(B303)

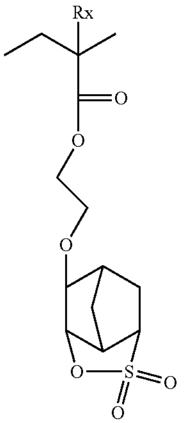

-continued (B304)

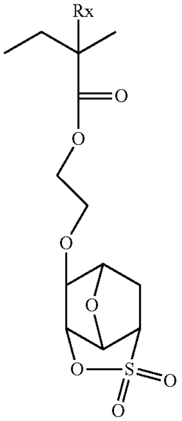

(B305)

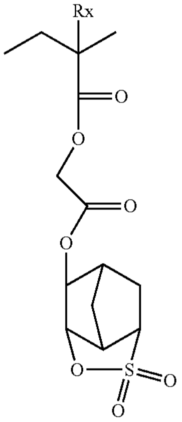

(B306)

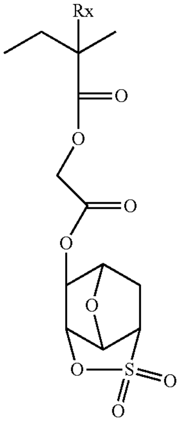

In the formulae, Rx represents H, $CH_3$, or $CF_3$.

(Repeating Unit (C))

The repeating unit (C) is a repeating unit having a hydroxy group or a carboxy group in a side chain, and imparts functions to improve the adhesion of the polymer to a substrate or an underlying film, to control the solubility in a solvent for lithography or an alkali developer, and to react with a curing agent to form a crosslinked structure.

Particularly preferred structures of the repeating unit (C) are the structures represented by the formulae (C1) to (C3).

[Chem 8]

(C1)

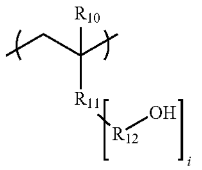

In the formula (C1), $R_{10}$ represents a hydrogen atom, or a $C_{1-4}$ hydrocarbon group that is optionally substituted with a fluorine atom, specifically including a hydrogen atom, or a $C_{1-4}$ alkyl group that is optionally substituted with a fluorine atom, such as a methyl, ethyl, n-propyl, i-propyl, n-butyl, i-butyl, or trifluoromethyl group, and is preferably a hydrogen atom, a methyl group, or a trifluoromethyl group. $R_{11}$ represents a substitute or unsubstituted aromatic hydrocarbon group. $R_{12}$ represents a single bond, a $C_{1-4}$ divalent hydrocarbon group that is optionally substituted with a fluorine atom, or a carbonyl group, specifically including a single bond, or a $C_{1-4}$ alkylene group that is optionally substituted with a fluorine atom, such as a methylene, 1,1-ethylene, 2,2-propylene, 1,1,1,3,3,3-hexafluoro-2,2-propylene, or 1,1,1-trifluoro-2-trifluoromethyl-2,3-propylene group, and is preferably a single bond, a 1,1,1,3,3,3-hexafluoro-2,2-propylene group, or a 1,1,1-trifluoro-2-trifluoromethyl-2,3-propylene group, and particularly preferably a single bond. i represents an integer of 1 or 2.

[Chem 9]

(C2)

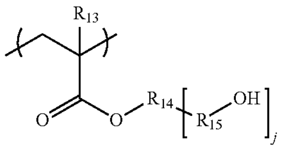

In the formula (C2), $R_{13}$ represents a hydrogen atom, or a $C_{1-4}$ hydrocarbon group that is optionally substituted with a fluorine atom, specifically including a hydrogen atom, or a $C_{1-4}$ alkyl group that is optionally substituted with a fluorine atom, such as a methyl, ethyl, n-propyl, i-propyl, n-butyl, i-butyl, or trifluoromethyl group, and is preferably a hydrogen atom, a methyl group, or a trifluoromethyl group. $R_{14}$ represents a $C_{2-14}$ di- to tetra-valent hydrocarbon group that optionally contains a fluorine atom, an oxygen atom, or a sulfur atom, specifically including a $C_{2-4}$ linear or branched saturated hydrocarbon group, such as an ethylene or isopropylene group, or a $C_{5-14}$ saturated alicyclic hydrocarbon group that has a cyclohexane ring, a norbornane ring, a 7-oxa-norbornane ring, a 7-thia-norbornane ring, an adamantane ring, a tetracyclo[4.4.0.12,5.17,10]dodecane ring, or other ring, and optionally contains an oxygen atom or a sulfur atom, and is preferably a cyclohexane ring, a norbornane ring, or an adamantane ring. $R_{15}$ represents a single bond, or a $C_{1-4}$ divalent hydrocarbon group that is optionally substituted with a fluorine atom, specifically including a single bond, or a $C_{1-4}$ alkylene group that is optionally substituted with a fluorine atom, such as a methylene, 1,1-ethylene, 2,2-propylene, 1,1,1,3,3,3-hexafluoro-2,2-propylene, or 1,1,1-trifluoro-2-trifluoromethyl-2,3-propylene group, and is preferably a single bond, a 1,1,1,3,3,3-hexafluoro-2,2-propylene group, or a 1,1,1-trifluoro-2-trifluoromethyl-2,3-propylene group. In a particularly preferred combination, $R_{14}$ is an adamantyl group, and $R_{15}$ is a single bond. j represents an integer of 1 to 3.

[Chem 10]

(C3)

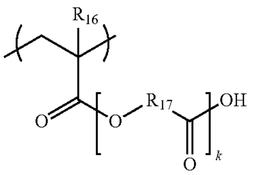

In the formula (C3), $R_{16}$ represents a hydrogen atom, or a $C_{1-4}$ hydrocarbon group that is optionally substituted with a fluorine atom, specifically including a hydrogen atom, or a $C_{1-4}$ alkyl group that is optionally substituted with a fluorine atom, such as a methyl, ethyl, n-propyl, i-propyl, n-butyl, i-butyl, or trifluoromethyl group, and is preferably a hydrogen atom, a methyl group, or a trifluoromethyl group. $R_{17}$ represents a $C_{6-12}$ divalent alicyclic hydrocarbon group that optionally contains an oxygen atom or a sulfur atom, specifically including an alicyclic hydrocarbon group that has a norbornane ring, a 7-oxa-norbornane ring, a 7-thia-norbornane ring, a tetracyclo[4.4.0.12,5.17,10]dodecane ring, or other ring, and optionally contains an oxygen atom or a sulfur atom; and is preferably a norbornane ring, or a tetracyclo[4.4.0.12,5.17,10]dodecane ring. k represents an integer of 0 or 1.

Specific examples of the repeating unit (C) will be described below, but the present invention is not limited thereto. One, or two or more having different structures may be selected from the repeating units (C) and used.

[Chem 11]

(C101)

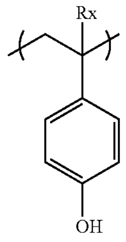

(C102)

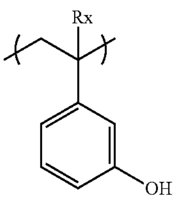

-continued
(C103)
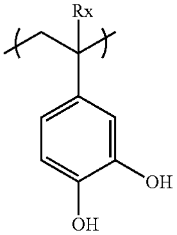
(C104)
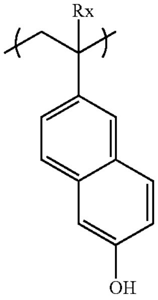
(C105)
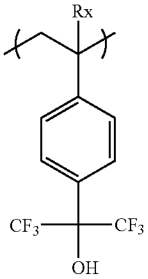
(C201)
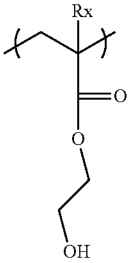
(C202)
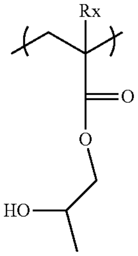
-continued
(C203)
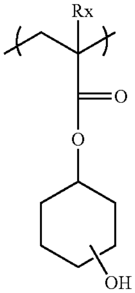
(C204)
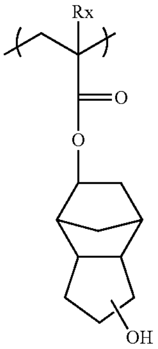
(C205)
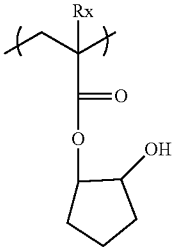
(C206)
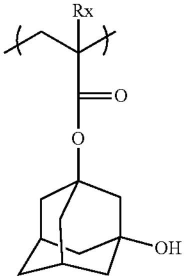
(C207)
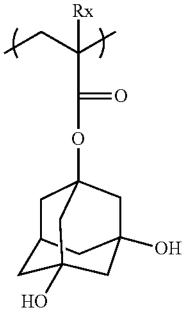

-continued (C208)

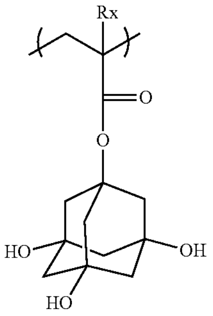

(C209)

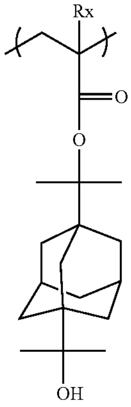

(C210)

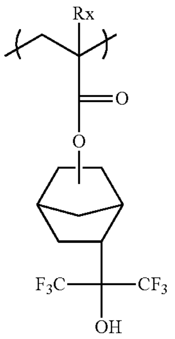

(C211)

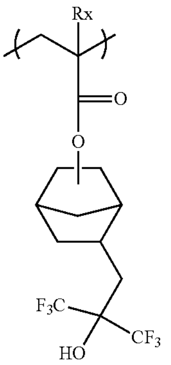

-continued (C301)

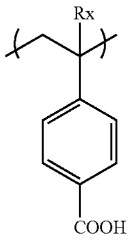

(C302)

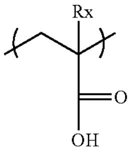

(C303)

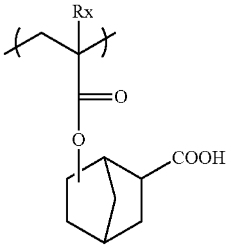

(C304)

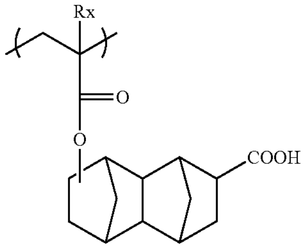

In the formulae, Rx represents H, $CH_3$, or $CF_3$.

(Repeating Unit (D))

The repeating unit (D) is a repeating unit having a structure in which an alkali-soluble group, such as a carboxyl group or a phenolic hydroxy group, is protected by an acid-stable dissolution inhibiting group that is not dissociated by the action of an acid. Preferably, the repeating unit (D) is a repeating unit in which a carboxyl group or a phenolic hydroxy group in a repeating unit derived from (meth)acrylic acid, hydroxystyrene, or the like is protected by an acid-stable dissolution inhibiting group. This repeating unit imparts functions, for example, to control the solubility in solvents for lithography or alkali developers, and the optical properties of films, such as refractive index and light transmittance.

The acid-stable dissolution inhibiting group may be a $C_{1-12}$ aliphatic hydrocarbon group, an aromatic hydrocarbon group, or a structure in which a methyl group and a 1-adamantyl group are bound, wherein the carbon bound to an oxygen atom after replacement of a hydrogen atom in a carboxyl group or a phenolic hydroxy group is primary or secondary carbon. Specific examples include methyl, ethyl, n-propyl, i-propyl, n-butyl, i-butyl, cyclopentyl, cyclohexyl, 2-norbornyl, 2-isobornyl, 8-tricyclo[5.2.1.02,6]decanyl, 1-adamantyl, 2-adamantyl, 4-tetracyclo[4.4.0.12,5.17,10]dodecanyl, phenyl, benzyl, naphthyl, and anthracenyl.

Specific examples of the repeating unit (D) will be described below, but the present invention is not limited thereto. One, or two or more having different structures may be selected from the repeating units (D) and used.

[Chem 12]

(D101)

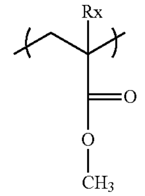

(D102)

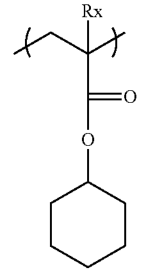

(D103)

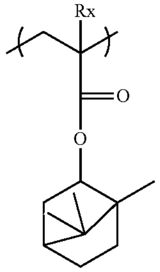

(D104)

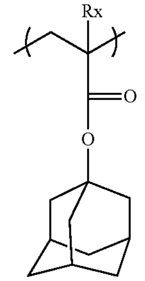

(D105)

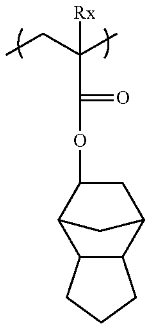

-continued (D106)

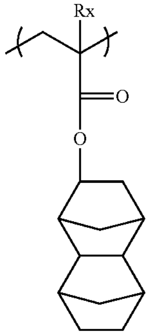

(D107)

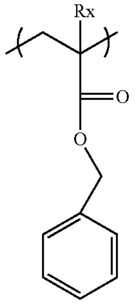

(D108)

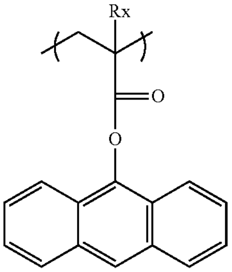

(D109)

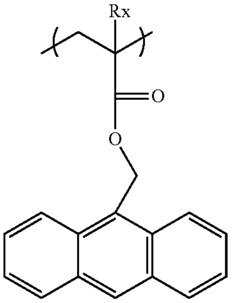

In the formulae, Rx represents H, $CH_3$, or $CF_3$.

An exemplary repeating unit having the same effect as the repeating unit (D) may be a repeating unit represented by the formula (D').

[Chem 13]

(D')

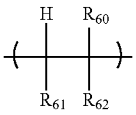

In the formula (D'), $R_{60}$ represents a hydrogen atom, or a $C_{1-4}$ hydrocarbon group that is optionally substituted with a fluorine atom, specifically including a hydrogen atom, or a $C_{1-4}$ alkyl group that is optionally substituted with a fluorine atom, such as a methyl, ethyl, n-propyl, i-propyl, n-butyl, i-butyl, or trifluoromethyl group, and is preferably a hydrogen atom, a methyl group, or a trifluoromethyl group. $R_{61}$ is a hydrogen atom, or a single bond or a $C_{1-4}$ alkylene group that will be bound to $R_{62}$, specifically including a hydrogen atom, a single bond, a methylene group, an ethylene group, or an isopropylene group. $R_{62}$ is a $C_{6-14}$ aromatic hydrocarbon group, specifically including a benzene ring, a naphthalene ring, or an anthracene ring.

Specific examples of the repeating unit (D') will be described below.

[Chem 14]

(D'101)

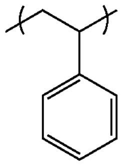

(D'102)

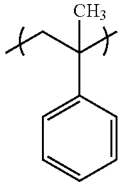

(D'203)

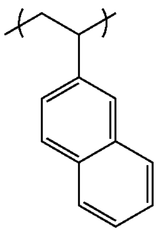

(D'204)

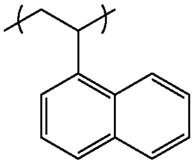

(D'205)

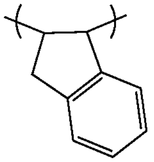

(D'206)

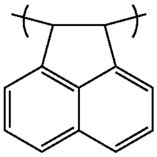

For polymerization, a conventionally known polymerization method can be applied, such as radical polymerization, cationic polymerization, or anionic polymerization.

The radical polymerization is carried out by stirring under heat source monomers, radical polymerization initiators, optionally chain transfer agents, and the like dissolved in a solvent, preferably under an inert gas atmosphere, such as nitrogen. For example, the radical polymerization can be performed by so-called batch polymerization in which all materials such as monomers, polymerization initiators, and chain transfer agents are dissolved in a solvent and heated to the polymerization temperature, or so-called droplet polymerization in which monomers, polymerization initiators, and the like are dissolved in a solvent to obtain a solution, which is then added dropwise to a solvent that is heated to the polymerization temperature. Especially, the droplet polymerization is preferable because of high reproducibility across production lots, and so-called independent droplet polymerization in which monomers and polymerization initiators that are sources of radicals are separately added dropwise is particularly preferable. Parts of the monomers, polymerization initiators, chain transfer agents, and the like can previously be fed in the polymerization system. In droplet polymerization, changing the composition and the rate of feed of each feed solution depending on the monomer concentration and composition, the radical concentration, and the like in the polymerization system allows for controlling the molecular weight distribution and composition distribution of the copolymer.

The radical polymerization initiators may be those that are conventionally known. Preferred examples of the radical polymerization initiators include azo compounds and peroxides. Specific examples of the polymerization initiators that are azo compounds include 2,2'-azobisisobutyronitrile, 2,2'-azobis(2-methylbutyronitrile), dimethyl 2,2'-azobis(2-methylpropionate), 1,1'-azobis(cyclohexane-1-carbonitrile), and 4,4'-azobis(4-cyanovaleric acid). Specific examples of the polymerization initiators that are peroxides include decanoyl peroxide, lauroyl peroxide, benzoyl peroxide, bis (3,5,5-trimethylhexanoyl) peroxide, succinic acid peroxide, tert-butylperoxy-2-ethylhexanoate, tert-butylperoxypivalate, and 1,1,3,3-tetramethylbutylperoxy-2-ethylhexanoate. These can be used alone or in combination.

The amounts of the polymerization initiators to be used can be selected depending on, for example, the intended molecular weight, the types of the monomers, polymerization initiators, chain transfer agents, solvents, and the like, the repeating unit composition, the polymerization temperature, and the dropping rate.

The chain transfer agents may be those that are known as chain transfer agents, as necessary. Especially, thiol compounds are preferable, which can be widely selected from known thiol compounds. The amounts of the chain transfer agents to be used can be selected depending on, for example, the intended molecular weight, the types of the monomers, polymerization initiators, chain transfer agents, solvents, and the like, the repeating unit composition, the polymerization temperature, and the dropping rate.

The solvent used in the polymerization reaction is not particularly limited as long as it is a solvent that can stably dissolve the monomers, polymerization initiators, chain transfer agents, and polymerization reaction products. Specifically, those illustrated as the solvent of the 4-hydroxystyrene solution described above can be used. These may be used alone or in combination of two or more.

The amount of the polymerization solvent to be used is not particularly limited. However, too small amount of the solvent used may result in deposition of monomers or inability of maintaining the uniformity of the polymerization system due to its excessively high viscosity, while too high amount may result in insufficient monomer conversion rate, or inability of increasing the molecular weight of the copolymer to a desired value. Usually, the amount is from 0.5 to 20 parts by weight relative to 1 part by weight of the monomers, preferably from 1 to 10 parts by weight.

The amount of the polymerization solvent with which the reactor is initially filled (hereinafter may be referred to as "initially filled solvent") is not limited as long as it is not less than the minimum amount that allows for stirring. However, a higher amount than necessary is undesirable because it reduces the amount of a monomer solution that can be supplied and lowers the production efficiency. Usually, the volume ratio of the amount to the final preparation amount (i.e., the total amount of the initially filled solvent, and the monomer solution and initiator solution added dropwise) is, for example, selected from a range of 1/30 or more, preferably from 1/20 to 1/2, and particularly preferably from 1/10 to 1/3. A part of the monomer and/or the polymerization initiator may be previously mixed with the initially filled solvent.

It is not desirable to add the monomer solution dropwise over a short period of time, because the molecular weight distribution tends to be wider, and because the temperature of the polymerized solution drops due to a large amount of solution being dropped at one time. On the other hand, addition over a long period of time is not desirable because the copolymer experiences more thermal history than necessary, and the productivity is reduced. Thus, the period of time is usually selected from 0.5 to 24 hours, preferably from 1 to 12 hours, and particularly preferably from 2 to 8 hours.

After completion of the dropwise addition, maturation by, for example, maintaining the temperature for a certain period of time or further increasing the temperature is preferably made to allow the remaining unreacted monomer to react. Maturation over a too long period of time is not desirable because the production efficiency per hour is reduced, and the copolymer experiences more thermal history than necessary. Thus, the period of time of maturation is usually selected from a range of 12 hours or less, preferably 6 hours or less, and particularly preferably from 1 to 4 hours.

The polymerization temperature can be appropriately selected depending on, for example, the boiling points of the solvent, monomer, chain transfer agent, and the like, and the half-life temperature of the polymerization initiator. The polymerization temperature is preferably selected from 40 to 160° C., and particularly preferably from 60 to 120° C. The polymerization temperature is required to be precisely controlled because it greatly affects the molecular weight of the copolymer and the copolymer composition. However, the polymerization reaction is generally an exothermic reaction, and thus it is difficult to control the temperature at a constant value. For this reason, at least one or more compound having a boiling point near the target polymerization temperature is preferably contained as a polymerization solvent, and the polymerization temperature is preferably set as the initial boiling point or higher of the compound at a polymerization pressure. According to this method, latent heat of vaporization of the polymerization solvent can inhibit the increase in the polymerization temperature.

The polymerization pressure can be set as appropriate. Since radical generation from the initiator results in generation of nitrogen gas when using an azo initiator, or oxygen gas when using a peroxide initiator, the polymerization system is preferably an open system and operated at near atmospheric pressure to prevent the polymerization pressure from being changed.

The polymer after the polymerization reaction exists with low molecular weight impurities such as the polymerization solvent, an unreacted monomer, oligomers, the polymerization initiator, and the chain transfer agent, as well as reaction byproducts thereof, which are preferably removed by a purification step. Specifically, the purification step is carried out by diluting the polymerization reaction solution with a good solvent as necessary; contacting the copolymer with a poor solvent to precipitate it as a solid; and extracting impurities into the poor solvent phase (hereinafter, referred to as "reprecipitation"), or into the poor solvent phase as a liquid-liquid two phase. In the case of reprecipitation, further purification can be made by a step of separating the precipitated solid from the poor solvent by filtration, decantation, or other method, then redissolving the solid in a good solvent, and further adding a poor solvent for reprecipitation, or by a step of washing the precipitated solid with a poor solvent. In the case of liquid-liquid two phase separation, further purification can be made by separating the poor solvent phase by a separating operation, and then adding a poor solvent to the obtained copolymer solution for reprecipitation, or subjecting the obtained copolymer solution to liquid-liquid two phase separation. The same operation may be repeated, or different operations may be combined.

The poor solvent used in the purification step may be, for example, water, a compound having a hydroxy group, such as methanol, ethanol, isopropanol, ethylene glycol, or ethyl lactate; a linear, branched, or ring saturated hydrocarbon, such as pentane, n-hexane, iso-hexane, n-heptane, cyclopentane, or methylcyclohexane; or an aromatic hydrocarbon such as toluene or xylene. These solvents may be used alone or in combination of two or more. The good solvent may be, for example, the polymerization solvent described above or a solvent illustrated as a film forming solvent described below, and the good solvent may be used in combination with a poor solvent.

The type and amount of the poor solvent used in the purification step are not particularly limited as long as it can separate the copolymer from low molecular weight compounds, and can be appropriately selected depending on, for example, the solubility of the copolymer in the poor solvent, the type and amount of the solvent used in polymerization, and the types and amounts of impurities. When the amount of the poor solvent is small, the impurities such as the polymerization solvent and the unreacted monomer is insufficiently separated. Conversely, too large amount results in, for example, increased waste fluid, and is not desirable in terms of workability and cost. The amount of the poor solvent is generally from 0.5 to 50 times by weight relative to the total amount of the polymerization reaction solution diluted with a good solvent as necessary, preferably from 1 to 20 times, and more preferably from 2 to 10 times.

The temperature during the purification step is required to be strictly controlled because it greatly affects, for example, the molecular weights and the molecular weight distribution of the copolymers, the removal rate of the impurities such as the remaining monomer and the residual initiator, and various properties in lithography. The purification step is inefficient at too low temperature because of insufficient solubility of the impurities to the solvent for reprecipitation and the solvent for washing and insufficient removal of the impurities. On the other hand, too high temperature is not desirable because the copolymers will be eluted in the solvent for reprecipitation and the solvent for washing, resulting in loss of balance in the copolymer composition in the low molecular weight region, and yield loss. Thus, it is desirable to perform the purification step at a temperature ranging from 0 to 40° C., preferably from 0 to 30° C.

Treatments to remove metallic impurities contained in the polymer may be performed. As a method therefor, a solution of the polymers dissolved in an organic solvent may be washed with pure water, may be contacted with an ion exchange resin, or may be filtered through an ion exchange filter. These methods may be performed in combination. The ion exchange resin and the ion exchange filter to be used may be known commercially-available products used for metal removal in resist polymers.

The purified polymer may be dried to prepare a powder, or may be redissolved in a good solvent before or after drying to prepare a solution. Alternatively, the solvent in the polymer solution is preferably replaced with a solvent that is used for resist compounds and the like by the method described below to prepare a polymer solution.

In the replacement method, the polymer solution was heated under reduced pressure to remove by evaporation low-boiling-point materials, such as the solvent used for purification, and a solvent for resist is supplied to the resulting product while further removing by evaporation the initial solvent and the supplied solvent together. Low-boiling-point impurities such as the solvent used in purification are removed to prepare a copolymer solution for resist.

The temperature of the heat source during heating under reduced pressure is not particularly limited as long as the temperature does not cause denaturation of the copolymer, and is usually preferably 100° C. or lower, more preferably 70° C. or lower, still more preferably 60° C. or lower, and particularly preferably 50° C. or lower. In the solvent replacement step, the copolymer solution during the step is cooled by heat of vaporization to a temperature that is lower than that of the heat source, to evaporate low-boiling-point components and the finishing solvent at under reduced pressure. Limitation of the temperature of the heat source can prevent deterioration of the copolymer due to overheating.

Too small amount of the solvent that is supplied later during solvent replacement is not desirable because of insufficient removal of low-boiling-point compounds, while too large amount is not desirable because it results in taking long time for replacement, giving more thermal history than necessary to the copolymer. The amount supplied can be selected from amounts in the range of usually 1.05 times to 10 times the amount needed as the solvent for the finished solution, preferably 1.1 times to 5 times, and particularly preferably 1.2 times to 3 times.

The replacement solvent is not particularly limited as long as it dissolves the copolymer. For resist applications, known solvents that are used in resist compositions can be usually used. Specific examples include solvents such as propylene glycol monomethyl ether acetate, propylene glycol monomethyl ether, propylene glycol n-butyl ether, dipropylene glycol n-propyl ether, dipropylene glycol n-butyl ether, ethyl lactate, methyl amyl ketone, γ-butyrolactone, cyclohexanone, and 4-methyl-2-pentanol.

Further, the copolymer solution (or the film forming solution described above) is preferably filtered through a filter to remove microgels such as high polymers that are not desirable because they cause resist pattern defects. The filter rating of the filter is 0.2 μm or less, preferably 0.1 μm or less, and particularly preferably 0.05 μm or less. The material of the filter may be, for example, polyolefin such as polyethylene or polypropylene, a polar group-containing resin such as polyamide, polyester, or polyacrylonitrile, or a fluorine-containing resin such as fluorinated polyethylene, and is particularly preferably polyamide. Examples of polyamide filters include (the names below are trademarks) ULTIPLEAT P-NYLON 66 and ULTIPOR N66 manufactured by Pall Corporation, and LifeASSURE PSN series and LifeASSURE EF series manufactured by Cuno Inc. Examples of polyolefin filters include MICROGARD PLUS HC10 and OPTIMIZER D manufactured by Nihon Entegris Co., Ltd. These filters may be used alone or in combination or two or more.

Preferably, polymers obtained by the production method of the present invention show highly reduced contamination of metals. Specifically, the total metal content is preferably 50 ppb or less, more preferably 10 ppb or less, and still more preferably 3 ppb or less on a polymer mass basis. Particularly preferably, all metals are in amounts that are not more than the detection limit of the analyzer.

The metal content is measured by inductively coupled plasma mass spectrometry (ICP-MS).

The metal content is typically the total of the amounts of Na, K, Mg, Al, Ca, Cr, Mn, Fe, Ni, Cu, Zn, Pb, Sn, Co, Li, Ti, Ag, W, V, Ba, Pt, Au, As, Cd, Mo, and Zr. Preferably, the amounts of the metals described above are 1 ppb or less.

[Evaluation Method of Insoluble or Slightly Soluble Components]

Insoluble or slightly soluble components contained in the polymer solution can be analyzed by the following steps.

Step (i): the polymer solution is diluted with a good solvent, followed by preparation of a test solution with a polymer concentration of 10.0 mass %.

Step (ii): the test solution is placed in a flask of a non-contact turbidimeter for rotary shaking culture (a shaker NR-2 equipped with OD MonitorA&S manufactured by Taitec Corporation is used), and a poor solvent is added dropwise at a constant rate with rotary shaking, during which change in the weight and change in the turbidity at a measurement wavelength of 950 nm of the test solution are recorded.

Step (iii): the addition of the poor solvent is continued until the turbidity is 0.20 OD (Optical Density). During the addition, the amounts of the poor solvent added until the turbidity reaches 0.10 OD, 0.15 OD, and 0.20 OD are recorded.

From the steps described above, a smaller amount of the poor solvent added until each turbidity is achieved indicates a smaller amount of insoluble or slightly soluble components.

A method of evaluating the insoluble or slightly soluble components described above can be applied for the 4-hydroxystyrene polymer solution described above and other polymer solutions.

EXAMPLES

Embodiments of the present invention will be described in detail with reference to the examples, but the present invention is not limited to the examples in any way. Unless not stated otherwise, parts are on a mass basis in the examples below.

Analyses in the examples were performed as described below. [Purity of 4-hydroxystyrene Solution] and [Weight Average Molecular Weight and Molecular Weight Distribution of Polymer]

The purity of a 4-hydroxystyrene solution, the amount of a polymer, and the weight average molecular weight and the molecular weight distribution of a polymer synthesized below were measured by GPC (gel permeation chromatography) using polystyrene as a standard. Samples for analysis were used, which were prepared to obtain a tetrahydrofuran solution with a solid content concentration of the polymer is 2 mass %. The amount of a sample injected into the equipment was 50 μL.

Measurement equipment: HLC-8220GPC manufactured by Tosoh Corporation

Detector: differential refractive index (RI) detector
Column: Shodex GPC KF804×3 (Showa Denko K.K.)
Eluent: tetrahydrofuran
Flow rate: 1.0 mL/min
Temperature: 40° C.
Calibration curve: prepared using a polystyrene standard sample (Tosoh Corporation)

[Water Content of 4-hydroxystyrene Solution]

The water content of the 4-hydroxystyrene solution synthesized below was measured using the following equipment:

Measurement equipment: Karl-Fisher trace water measurement equipment AQ-7 (Hiranuma Co., Ltd.)

[Determination of Amount of Low Molecular Weight Component in Polymer]

Low molecular weight components contained in the polymer synthesized below were analyzed for quantitative determination by LC (liquid chromatography).

Measurement equipment: HLC-8320GPC manufactured by Tosoh Corporation
Detector: differential refractive index (RI) detector
Column: TSKgel superHZ1000×4 manufactured by Tosoh Corporation
Eluent: tetrahydrofuran
Flow rate: 0.35 mL/min
Temperature: 40° C.

[Monomer Composition Ratio of Polymer]

The monomer composition ratios of polymers synthesized below were analyzed by $^{13}C$-NMR.

Machine: AV400 manufactured by Bruker
Deuterated solvent: acetone-d6
Relaxation reagent: chromium (III) acetylacetonate
Measurement temperature: 40° C.

[Analysis of Metal in Polymer Solution]

The metal contents in the polymers synthesized below were analyzed by inductively coupled plasma mass spectrometry (ICP-MS). Measured metals were a total of 26 elements, Na, K, Mg, Al, Ca, Cr, Mn, Fe, Ni, Cu, Zn, Pb, Sn, Co, Li, Ti, Ag, W, V, Ba, Pt, Au, As, Cd, Mo, and Zr. The analytical values are on a mass basis for the polymer solid contents.

Machine: ICP mass spectrometer (product name: Agilent 7500cs, manufactured by Agilent Technologies, Inc.)
Sample preparation: Polymer solutions were diluted with N-methyl-2-pyrrolidone.

The abbreviated names of the compounds used in the following experiments are as follows:

PACS: p-acetoxystyrene
4-HS: 4-hydroxystyrene
MCpMA: 1-methyl-1-cyclopentyl methacrylate
ECpMA: 1-ethyl-1-cyclopentyl methacrylate
TBMA: tert-butyl methacrylate
GBLMA: γ-butyrolactone-α-methacrylate
NLM: 3,5-norbornanelacton-2-yl-methacrylate
MEK: methyl ethyl ketone
MTBE: methyl tertiary butyl ether
PGMEA: propylene glycol monomethyl ether acetate
PGME: propylene glycol monomethyl ether
MeOH: methanol
IPA: 2-propanol
SBA: 2-butanol
EtOAc: ethyl acetate
THF: tetrahydrofuran <Method of Producing 4-hydroxystyrene Solution>

Example 1

To a 100-L glasslined reactor equipped with a thermometer, a condenser, and a stirrer were added 7.9 kg of PACS and 23.4 kg of methanol, followed by nitrogen sealing. The content was cooled to a liquid temperature of −5° C. with stirring. Thereafter, the pressure inside the reactor was reduced and recovered with nitrogen, which operations were repeated three times. In another chamber than the reactor, an aqueous solution of 3 M sodium hydroxide equimolar to PACS was prepared, which aqueous solution was then subjected to bubbling with nitrogen for 1 hour. The aqueous solution of sodium hydroxide after nitrogen bubbling was added dropwise to the reactor for 100 minutes, and then was kept stirred for another 30 minutes, followed by a reaction for deprotection of PACS to convert it to 4-HS.

Then, 0.97 molar equivalent of 6M hydrochloric acid relative to the used PACS was added dropwise to the reactor for 60 minutes, and then was kept stirred for another 30 minutes to neutralize the reaction solution. The 6M hydrochloric acid that was added dropwise had been previously bubbled with nitrogen for 1 hour.

Then, the temperature of the neutralized reaction solution was raised to about 10 to 20° C., to which MTBE with a mass 3 times that of PACS was added and stirred for 15 minutes. After leaving the mixture to stand for 15 minutes, the aqueous layer was drained. Then, ion exchanged water with a mass 3 times that of PACS was added and stirred for 15 minutes. After leaving the mixture to stand for 15 minutes, the aqueous layer was drained. Then, MTBE and ion exchanged water with masses 2 and 3 times that of PACS, respectively, were added and stirred for 15 minutes. After leaving the mixture to stand for 15 minutes, the aqueous layer was drained. Finally, ion exchanged water with a mass 3 times that of PACS was added, stirred for 15 minutes, left to stand for 15 minutes, followed by draining of the aqueous layer, which operations were repeated twice.

The organic layer after washing was transferred to another 100-L reactor, to which MEK with a mass 13 times that of the initial PACS was added. The mixture was distilled at 25° C. or lower under a reduced pressure of 5 kPa to evaporate off organic impurities other than 4-HS, such as tert-butyl methyl ether and reaction byproducts, and excess MEK and finally obtain a solution containing 4-HS in a concentration of 25 mass %. Then, the solution was allowed to pass through a polytetrafluoroethylene (PTFE) hollow fiber membrane filter with a pore size of 50 nm to obtain 21 kg of 25 mass % 4-HS/MEK solution (yield: 92%).

A part of the obtained 4-HS solution was aliquoted to a plurality of vessels for preservation test at temperatures of −15° C., −5° C., and 40° C. In the preservation test, 4-HS and polymers in the 4-HS solution immediately, 20 days, 40 days, 90 days, and 180 days after production were analyzed by gel permeation chromatography (GPC). The results are shown in Table 1.

TABLE 1

| | solvent | 4-HS Concentration (wt %) | Water Content (wt %) | storage temperature (° C.) | % of GPC areas: 4-HS/polymer days elapsed 0 days | 20 days | 40 days | 90 days | 180 days |
|---|---|---|---|---|---|---|---|---|---|
| Ex. 1 | MEK | 25 | 0.03 | −15 | 99.95/ 0.05 | 99.93/ 0.07 | 99.94/ 0.06 | 99.97/ 0.03 | 99.90/ 0.10 |
| | | | | 5 | | 99.90/ 0.10 | 99.89/ 0.11 | 99.65/ 0.35 | 99.34/ 0.66 |
| | | | | 40 | | 99.62/ 0.38 | 98.85/ 1.15 | No data | No data |

The 25 mass % 4-HS/MEK solution obtained in Example 1 could be stably stored at −15° C. for 6 months with little polymerization. In the accelerated test at 40° C., production of polymers could also be kept below 0.5% for up to 20 days.

Example 2

To a four-necked flask equipped with a thermometer, a condenser, and a stirrer were added 53.52 g of PACS and 160.5 g of methanol, followed by nitrogen sealing. The content was cooled to a liquid temperature of −5° C. with stirring. Thereafter, the pressure inside the reactor was reduced and recovered with nitrogen, which operations were repeated three times. In another chamber than the reactor, an aqueous solution of 3 M sodium hydroxide was prepared so that it was equimolar to PACS, and then the aqueous solution was subjected to bubbling with nitrogen for 15 minutes. The aqueous solution of sodium hydroxide after nitrogen bubbling was added dropwise to the reactor for 70 minutes, and then was kept stirred for another 30 minutes, followed by a reaction for deprotection of PACS to convert it to 4-HS.

Then, 0.97 molar equivalent of 6 N hydrochloric acid relative to the used PACS was added dropwise to the reactor for 45 minutes, and then was kept stirred for another 30 minutes to neutralize the reaction solution. The 6 N hydrochloric acid that was added dropwise had been previously bubbled with nitrogen for 1 hour.

Then, the temperature of the neutralized reaction solution was raised to about 10 to 20° C., to which MTBE with a mass 3 times that of PACS was added and stirred for 15 minutes. After leaving the mixture to stand for 15 minutes, the aqueous layer was drained. Then, ion exchanged water with a mass 3 times that of PACS was added and stirred for 15 minutes. After leaving the mixture to stand for 15 minutes, the aqueous layer was drained. Then, MTBE and ion exchanged water with masses 2 and 3 times that of PACS, respectively, were added and stirred for 15 minutes. After leaving the mixture to stand for 15 minutes, the aqueous layer was drained. Finally, ion exchanged water with a mass 3 times that of PACS was added, stirred for 15 minutes, left to stand for 15 minutes, followed by draining of the aqueous layer, which operations were repeated twice.

The organic layer after washing was transferred to another reactor, to which MEK with a mass 13 times that of the initial PACS was added. The mixture was distilled at 25° C. or lower under a reduced pressure to evaporate off organic impurities other than 4-HS, such as MTBE and reaction byproducts, and excess MEK and finally obtain a solution containing 4-HS in a concentration of 50 mass %. Then, the 4-HS solution was allowed to pass through a polytetrafluoroethylene (PTFE) membrane filter with a pore size of 50 nm.

A part of the obtained 4-HS solution was aliquoted to vessels for preservation test at −15° C. In the preservation test, 4-hydroxylene and polymers in the 4-HS solution immediately and 30 days after production were analyzed by GPC. The results are shown in Table 2.

TABLE 2

| | solvent | 4-HS concentration (wt %) | water content (wt %) | storage temperature (° C.) | % of GPC areas: 4-HS/polymer days elapsed 0 days | 30 days |
|---|---|---|---|---|---|---|
| Ex. 2 | MEK | 50 | 0.03 | −15 | 99.90/ 0.10 | 99.90/ 0.10 |

Example 3

The same experiment as Example 2 was performed, expect that propylene glycol methyl ether acetate (hereinafter, referred to as "PGMEA") was used instead of MEK as a replacement solvent, to finally obtain a 25 mass % 4-HS/PGMEA solution.

A part of the obtained 4-HS solution was aliquoted to vessels for preservation test at −15° C. 4-HS and polymers in the 4-HS solution immediately and 30 days after production were analyzed by GPC. The results are shown in Table 3.

TABLE 3

| | solvent | 4-HS concentration (wt %) | water content (wt %) | storage temperature (° C.) | % of GPC areas: 4-HS/polymer days elapsed 0 days | 30 days |
|---|---|---|---|---|---|---|
| Ex. 3 | PGMEA | 25 | 0.03 | −15 | 99.89/ 0.11 | 99.88/ 0.12 |

Comparative Example 1

A deprotection reaction, neutralization, and washing-off of PACS were performed in the same manner as in Example 2 to obtain a solution of 4-HS in MTBE. This solution was transferred to a 1-L grass vessel and distilled under reduced pressure at 20° C. or lower to evaporate off the solvent. The obtained polymer was further dried under reduced pressure at 40° C. for 4 hours to obtain 32 g of 4-HS crystals. Thereafter, the obtained 4-HS crystals were dissolved in MEK to prepare a 25 mass % 4-HS/MEK solution.

A part of the obtained 4-HS solution was aliquoted to vessels for preservation test at −15° C. 4-HS and polymers in the 4-HS solution immediately, 4 days, and 7 days after production were analyzed by GPC. The results are shown in Table 4.

TABLE 4

| | solvent | 4-HS concentration (wt %) | storage temperature (° C.) | % of GPC areas: 4-HS/polymer days elapsed 0 days | 4 days | 7 days |
|---|---|---|---|---|---|---|
| Com. Ex. 1 | MEK | 25 | −15 | 96.83/ 3.17 | 96.66/ 3.34 | 96.58/ 3.42 |

Comparative Example 1 was performed, without the solvent replacement step, by distillation under reduced pressure and drying under reduced pressure to remove a MTBE solvent, followed by dissolution of the obtained 4-HS crystals in MEK, to obtain a solution. This resulted in failure to prevent production of 4-HS polymers, as well as insufficient storage stability.

<Storage Stability Test of 4-hydroxystyrene Solution>

Example 4

A deprotection reaction with PACS, neutralization of the reaction solution, and washing were performed in the same manner as in Example 1 to obtain a solution of 4-HS in MTBE.

This solution in MTBE was concentrated in an evaporator till the concentration of 4-HS was 70 mass %, added dropwise to n-hexane at 0° C., and then stirred while cooling the bottom of the vessel with an ice bath to crystallize 4-HS. The collected 4-HS crystals were further washed with n-hexane, and dried under reduced pressure at room temperature.

A part of the obtained 4-HS crystals was dissolved in MEK to prepare a solution with a 4-HS concentration of 25 mass %. This was aliquoted into a plurality of vessels for storage stability test. The results are shown in Table 5.

[Example 5] to [Example 13]

4-HS crystals were synthesized in the same manner as in Example 4, and 4-HS solutions were prepared with the solvents and concentrations set as shown in Table 5, and with the storage temperature controlled to −5° C., 15° C., or 40° C., for storage stability test. The results are shown in Table 5.

TABLE 5

| | solvent | 4-HS concentration (wt %) | water content (wt %) | storage temperature (° C.) | % of GPC areas: 4-HS/polymer days elapsed 0 days | 20 days | 40 days | 90 days | 180 days |
|---|---|---|---|---|---|---|---|---|---|
| Ex. 4 | MEK | 25 | 0.03 | −15 | 99.87/ 0.13 | 99.85/ 0.15 | 99.92/ 0.08 | 99.89/ 0.11 | 99.82/ 0.18 |
| | | | | 5 | | 99.82/ 0.18 | 99.81/ 0.19 | 99.57/ 0.43 | 99.26/ 0.74 |
| Ex. 5 | MEK | 35 | 0.03 | −15 | 99.88/ 0.12 | 99.81/ 0.19 | 99.90/ 0.10 | 99.85/ 0.15 | 99.66/ 0.34 |
| Ex. 6 | MEK | 50 | 0.03 | −15 | 99.87/ 0.13 | 99.90/ 0.10 | 99.87/ 0.13 | 99.72/ 0.28 | 99.62/ 0.38 |
| | | | | 5 | | 99.86/ 0.14 | 99.82/ 0.18 | 99.78/ 0.22 | No data |
| | | | | 40 | | 99.80/ 0.20 | 99.59/ 0.41 | 99.27/ 0.73 | No data |
| Ex. 7 | MeOH | 50 | 0.03 | −15 | 99.66/ 0.34 | 99.56/ 0.44 | 99.34/ 0.66 | 99.39/ 0.61 | 99.25/ 0.75 |
| | | | | 5 | | none | 98.86/ 1.14 | 97.44/ 2.56 | 96.40/ 3.60 |
| Ex. 8 | IPA | 25 | 0.03 | −15 | 99.68/ 0.32 | 99.59/ 0.41 | 99.59/ 0.41 | 99.59/ 0.41 | 99.59/ 0.41 |
| | | | | 5 | | none | 99.56/ 0.44 | 99.44/ 0.56 | 99.14/ 0.86 |
| Ex. 9 | IPA | 50 | 0.03 | −15 | 99.63/ 0.37 | 99.49/ 0.51 | 99.41/ 0.59 | 99.40/ 0.60 | 99.42/ 0.58 |
| Ex. 10 | SBA | 25 | 0.03 | 5 | 99.50/ 0.50 | 99.50/ 0.50 | 99.42/ 0.58 | 99.30/ 0.70 | 98.83/ 1.17 |
| Ex. 11 | n-octanol | 25 | 0.03 | 5 | 99.60/ 0.40 | 99.46/ 0.54 | 99.40/ 0.60 | 99.02/ 0.98 | 98.37/ 1.63 |
| Ex. 12 | EtOAc | 25 | 0.03 | 5 | 99.58/ 0.42 | 99.32/ 0.68 | 99.39/ 0.61 | 99.30/ 0.70 | 98.70/ 1.30 |
| Ex. 13 | THF | 25 | 0.03 | 5 | 99.63/ 0.37 | 99.59/ 0.41 | 99.64/ 0.36 | 99.49/ 0.51 | 99.37/ 0.63 |

<Method of Producing 4-hydroxystyrene Polymer>

[Example 14] Production of 4-HS/MCpMA Copolymer

To a vessel were added 80.0 g of 25 mass % 4-HS/MEK solution obtained in Example 1 (the chromatogram area of 4-HS was 99.9% in GPC analysis when the total chromatogram area of components other than MEK was considered as 100), 45.6 g of MCpMA, 8.4 g of 2,2-azobisisobutyric acid dimethyl, and 13.0 g of MEK, and mixed to prepare a monomer solution.

A glass 500-mL four-necked flask reactor equipped with a stirrer, condenser, and thermometer was fed with 52.7 g of MEK, allowed to have nitrogen atmosphere, and then heated to 79° C. To the reactor, the monomer solution was fed dropwise for 4 hours at a constant rate, and the reaction was continued for additional 2 hours. The temperature during the polymerization reaction was controlled within 79.0 to 80.5° C., and then cooled to room temperature after the completion of polymerization.

The polymer solution was mixed with 460 g of n-hexane with stirring to precipitate a polymer, and then left to stand, followed by decantation to isolate the polymer. The polymer was redissolved in a mixed solution containing 40 g of acetone and 30 g of 2-propanol, to which 460 g of n-hexane was added with stirring to precipitate a polymer, followed by decantation to isolate the polymer, which operations were repeated four times. The collected polymer was dissolved in 140 g of ethyl acetate. A part of the polymer solution was sampled, and dried under reduced pressure at 40° C. to obtain powder of the polymer, which was then subjected to NMR analysis. The monomer composition ratio (molar ratio) of the polymer by the NMR analysis was 4-HS:MCpMA=41.0:59.0.

The remaining polymer solution was washed using a separatory funnel with 1 mass % aqueous oxalic acid solution, and then with pure water five times. The washed polymer solution was distilled while evaporating off ethyl acetate at a heat source temperature of 45° C. under reduced pressure and adding PGMEA, to finally obtain a solution of 4-HS/MCpMA copolymer with a polymer concentration of 15 mass % in PGMEA. The obtained polymer solution was analyzed by GPC and LC to find that Mw=5800, Mw/Mn=1.40, and remaining low molecular weight components with Mw of less than 200=0.01% (LC area %).

[Example 15] Production of 4-HS/MCpMA Copolymer

The same was performed as in Example 14 except that the capacity of the reactor used in the polymerization reaction was changed to 2 L, and that the amounts of the monomer, solvent, reagents, and the like used were changed to four times those in Example 14.

Analyses of the obtained polymer resulted in 4-HS:MCpMA=40.3:59.7, Mw=5810, Mw/Mn=1.39, and remaining low molecular weight components with Mw of less than 200=0.00% (LC area %).

[Example 16] Production of 4-HS/MCpMA Copolymer

The same was performed as in Example 14 except that the capacity of the reactor used in the polymerization reaction was changed to 10 L, and that the amounts of the monomer, solvent, reagents, and the like used were changed to 25 times those in Example 14.

Analyses of the obtained polymer resulted in 4-HS:MCpMA=40.5/59.5, Mw=5,800, Mw/Mn=1.40, and remaining low molecular weight components with Mw of less than 200=0.00% (LC area %).

The results from Examples 15 and 16 demonstrated that the present method could produce the polymer with good reproducibility of the properties even when the production scale was greatly changed.

[Example 17] Production of 4-HS/ECpMA Copolymer

To a vessel were added 400.0 g of 25.9 mass % 4-HS/MEK solution produced in the same manner as in Example 1 (the chromatogram area of 4-HS was 100.0% in GPC analysis when the total chromatogram area of components other than MEK was considered as 100), 280.6 g of ECpMA, 29.6 g of 2,2-azobisisobutyric acid dimethyl, and 86.0 g of MEK, and mixed to prepare a monomer solution.

A glass 2-L four-necked flask reactor equipped with a stirrer, condenser, and thermometer was fed with 302 g of MEK, allowed to have nitrogen atmosphere, and then heated to 79° C. To the reactor, the monomer solution was fed dropwise for 4 hours at a constant rate, and then the reaction was continued for additional 2 hours. The temperature during the polymerization reaction was controlled within 79.0 to 80.5° C., and then cooled to room temperature after the completion of polymerization.

Then, 1,000 g of the polymer solution was mixed with 2,300 g of n-hexane and 100 g of methanol with stirring to precipitate a polymer, and then left to stand, followed by decantation to isolate the polymer. The polymer was redissolved in a mixed solution of 200 g of acetone and 100 g of methanol, to which 2,000 g of n-hexane was added with stirring to precipitate a polymer, followed by decantation to isolate the polymer, which operations were repeated four times. The collected polymer was dissolved in 400 g of acetone. A part of the polymer solution was sampled, and dried under reduced pressure at 40° C. to obtain powder of the polymer, which was then subjected to NMR analysis. The monomer composition ratio (molar ratio) of the polymer by the NMR analysis was 4-HS:ECpMA=39.5:60.5.

The remaining polymer solution was distilled with acetone evaporated off at a heat source temperature of 45° C. under reduced pressure and with addition of PGMEA to replace the solvent with PGMEA, thereby finally obtaining a solution of 4-HS/ECpMA copolymer with a polymer concentration of 20 mass % in PGMEA. The obtained polymer solution was analyzed by GPC and LC to find that Mw=7430, Mw/Mn=1.46, and remaining low molecular weight components with Mw of less than 200=0.01% (LC area %).

[Example 18] Production of 4-HS/ECpMA Copolymer

Polymerization, purification, and solvent replacement were performed in the same manner as in Example 17 except that a 100-L glasslined reactor equipped with a stirrer, heat medium circulating jacket, vacuum line, nitrogen line, and condenser was used as a reactor used in the polymerization reaction, and that the amounts of the monomer, solvent, reagents, and the like used were changed to 55 times those in Example 17.

Analyses of the obtained polymer resulted in 4-HS: ECpMA=39.8:60.2, Mw=7450, Mw/Mn=1.46, and remaining low molecular weight components with Mw of less than 200=0.01% (LC area %).

ICP mass spectrometry to determine the metal contents in the solution of 4-HS/ECpMA copolymer with a polymer concentration of 20 mass % in PGMEA obtained in Example 18 resulted in 8 ppb of Na, and less than 1.0 ppb of all the other elements, based on the weight of the polymer.

The results from Examples 17 and 18 demonstrated that the present method could also be used to produce polymers with good reproducibility in the properties and with very little amount of low molecular weight impurities and metallic impurities in the case of production in a commercial scale.

[Comparative Example 2] Production of 4-HS/MCpMA Copolymer

The same was performed as in Example 15 except that a 25 mass % 4-HS/MEK solution (the chromatogram area of 4-HS was 97.3% in GPC analysis when the total chromatogram area of components other than MEK was considered as 100) was used.

Analyses of the obtained polymer resulted in 4-HS: MCpMA=40.4:59.6, Mw=5860, Mw/Mn=1.40, and remaining low molecular weight components with Mw of less than 200=0.00% (LC area %), which physical properties were the same as those of the polymer obtained in Example 15.

[Evaluation of Insoluble or Slightly Soluble Components]

For comparison of insoluble or slightly soluble components contained in the solutions of 4-HS/MCpMA copolymer in PGMEA obtained in Example 15 and Comparative Example 2, test solutions were prepared, and a poor solvent was added to the test solutions, during which the changes in the turbidities of the test solutions were measured in real time. The detailed testing method will be shown below.

For preparation of the test solutions, the polymer solutions obtained in Example 15 and Comparative Example 2 were further diluted with PGMEA, with the polymer concentration adjusted to 10.0 mass %, thereby obtaining the test solutions.

The turbidity was measured using a non-contact turbidimeter for rotary shaking culture (a shaker NR-2 equipped with OD-MonitorA&S manufactured by Taitec Corporation was used). A glass Erlenmeyer flask was charged with 100.0 g of the test solution, and the mouth of the Erlenmeyer flask was sealed with a plug having a tube for dropwise addition of a poor solvent to prevent evaporation of the solvent. A zero-point adjustment for the turbidimeter was performed while the Erlenmeyer flask containing the test solution was under rotary shaking. n-hexane as a poor solvent was added dropwise at a rate of 0.3 g/min with rotary shaking of the Erlenmeyer flask, during which change in the weight of the test solution and change in the turbidity of the test solution were measured. The measurement OD from the turbidimeter used in this case (optical density; OD=common logarithm of the transmittance of transmitted light) is the amount of transmitted infrared light (950 nm) converted to $OD_{600}$ for *E. coli*. The dropwise addition of n-hexane was continued until the turbidity was 0.50 OD. Visually, a thin turbidity was observed in the test solution with a turbidity of 0.50 OD, but no polymer precipitation was observed. The measurement was performed three times, and the average values of the amounts of n-hexane added dropwise in the three experiments until the turbidity reached 0.10 OD, 0.15 OD, 0.20 OD, 0.30 OD, and 0.50 OD were summarized in Table 1.

TABLE 6

| | source 4-HS (purity by GPC) | amount of n-hexane added dropwise*(g) 0.10 OD | 0.15 OD | 0.20 OD | 0.30 OD | 0.50 OD |
|---|---|---|---|---|---|---|
| Ex. 15 | 99.9% | 9.8 | 12.3 | 14.4 | 16.0 | 18.0 |
| Com. Ex. 2 | 97.3% | 7.5 | 10.6 | 12.6 | 16.2 | 18.4 |

*average value of three measurements

From the results obtained in the experiments, no difference was found between Example 15 and Comparative Example 2 for turbidity of 0.30 OD or more, but there found to be differences in the amounts of n-hexane added dropwise needed to cause turbid in a level from 0.10 OD to 0.20 OD, or very slight turbid, resulting in larger amount of n-hexane added dropwise in Example 15. The copolymer obtained in Example 15 can be evaluated to be almost the same as the copolymer obtained in Comparative Example 2 in terms of physical properties such as monomer composition ratio, Mw, Mw/Mn, and amounts of remaining low molecular weight components, but to have smaller amount of insoluble or slightly soluble components that can cause post-develop defects.

[Example 19] Production of 4-HS/MCpMA/GBLMA Copolymer

To a vessel were added 48.3 g of 25 mass % 4-HS/MEK solution obtained in Example 1 (the chromatogram area of 4-HS was 99.9% in GPC analysis when the total chromatogram area of components other than MEK was considered as 100), 55.5 g of MCpMA, 28.6 g of GBLMA, 6.9 g of 2,2-azobisisobutyric acid dimethyl, and 61.2 g of MEK, and mixed to prepare a monomer solution.

A glass 500-mL four-necked flask reactor equipped with a stirrer, condenser, and thermometer was fed with 74.8 g of MEK, allowed to have nitrogen atmosphere, and then heated to 79° C. To the reactor, the monomer solution was fed dropwise for 4 hours at a constant rate, and then the reaction was continued for additional 2 hours. The temperature during the polymerization reaction was controlled within 79.0 to 80.5° C., and then cooled to room temperature after the completion of polymerization.

Then, 275 g of the polymer solution was mixed with 620 g of n-hexane and 67 g of methanol with stirring to precipitate a polymer, and then left to stand, followed by decantation to isolate the polymer. The polymer was redissolved in a mixed solution containing 67 g of MEK and 67 g of methanol, to which 540 g of n-hexane was added with stirring to precipitate a polymer, followed by decantation to isolate the polymer, which operations were repeated twice.

The collected polymer was dissolved in 270 g of ethyl acetate. A part of the polymer solution was sampled, and dried under reduced pressure at 40° C. to obtain powder of the polymer, which was then subjected to NMR analysis. The monomer composition ratio (molar ratio) of the polymer by the NMR analysis was 4-HS:MCpMA:GBLMA=18.8:51.8:29.4.

The remaining polymer solution was washed using a separatory funnel with 1 mass % aqueous oxalic acid solution, and then with pure water five times. The washed polymer solution was distilled while evaporating off ethyl acetate at 45° C. under reduced pressure and adding PGMEA, to finally obtain a solution of 4-HS/MCpMA/GBLMA copolymer with a polymer concentration of 20 mass % in PGMEA. The obtained polymer solution was analyzed by GPC and LC to find that Mw=9720, Mw/Mn=1.59, and remaining low molecular weight components with Mw of less than 200=0.01% (LC area %).

[Example 20] Preparation of 4-HS/MCpMA/NLM Copolymer

To a vessel were added 52.8 g of 25 mass % 4-HS/MEK solution obtained in Example 1 (the chromatogram area of 4-HS was 99.9% in GPC analysis when the total chromatogram area of components other than MEK was considered as 100), 66.7 g of MCpMA, 24.5 g of NLM, 18.4 g of 2,2-azobisisobutyric acid dimethyl, and 61.7 g of MEK, and mixed to prepare a monomer solution.

A glass 500-mL four-necked flask reactor equipped with a stirrer, condenser, and thermometer was fed with 75.4 g of MEK, allowed to have nitrogen atmosphere, and then heated to 79° C. To the reactor, the monomer solution was fed dropwise for 4 hours at a constant rate, and then the reaction was continued for additional 2 hours. The temperature during the polymerization reaction was controlled within 79.0 to 80.5° C., and then cooled to room temperature after the completion of polymerization.

The polymer solution was mixed with 690 g of n-hexane with stirring to precipitate a polymer, and then left to stand, followed by decantation to isolate the polymer. The polymer was redissolved in a mixed solution containing 120 g of MEK and 45 g of methanol, to which 690 g of n-hexane was added with stirring to precipitate a polymer, followed by decantation to isolate the polymer, which operations were repeated four times.

The collected polymer was dissolved in 450 g of ethyl acetate. A part of the polymer solution was sampled, and dried under reduced pressure at 40° C. to obtain powder of the polymer, which was then subjected to NMR analysis. The monomer composition ratio (molar ratio) of the polymer by the NMR analysis was 4-HS:MCpMA:NLM=20.2:59.4:20.4.

The remaining polymer solution was washed using a separatory funnel with 1 mass % aqueous oxalic acid solution, and then with pure water five times. The washed polymer solution was distilled while evaporating off ethyl acetate at 45° C. under reduced pressure and adding PGMEA, to finally obtain a solution of 4-HS/MCpMA/NLM copolymer with a polymer concentration of 15 mass % in PGMEA. The obtained polymer solution was analyzed by GPC and LC to find that Mw=5240, Mw/Mn=1.39, and remaining low molecular weight components with Mw of less than 200=0.00% (LC area %).

[Example 21] Production of 4-HS/TBMA Copolymer

To a vessel were added 200.0 g of 25 mass % 4-HS/MEK solution obtained in Example 1 (the chromatogram area of 4-HS was 99.9% in GPC analysis when the total chromatogram area of components other than MEK was considered as 100), 81.8 g of TBMA, 16.8 g of 2,2-azobisisobutyric acid dimethyl, and 17.0 g of MEK, and mixed to prepare a monomer solution.

A glass 1000-mL four-necked flask reactor equipped with a stirrer, condenser, and thermometer was fed with 105.1 g of MEK, allowed to have nitrogen atmosphere, and then heated to 79° C. To the reactor, the monomer solution was fed dropwise for 4 hours at a constant rate, and then the reaction was continued for additional 2 hours. The temperature during the polymerization reaction was controlled within 79.0 to 80.5° C., and then cooled to room temperature after the completion of polymerization.

The polymer solution was mixed with 880 g of n-hexane and 20 g of methanol with stirring to precipitate a polymer, and then left to stand, followed by decantation to isolate the polymer. The polymer was redissolved in a mixed solution containing 176 g of acetone and 12 g of methanol, to which 800 g of n-hexane was added with stirring to precipitate a polymer, followed by decantation to isolate the polymer, which operations were repeated four times.

The collected polymer was dissolved in 180 g of acetone. A part of the polymer solution was sampled, and dried under reduced pressure at 40° C. to obtain powder of the polymer, which was then subjected to NMR analysis. The monomer composition ratio (molar ratio) of the polymer by the NMR analysis was 4-HS:TBMA=42.4:57.6.

The washed polymer solution was distilled while evaporating off acetone at 45° C. under reduced pressure and adding PGMEA, to finally obtain a solution of 4-HS/TBMA copolymer with a polymer concentration of 20 mass % in PGMEA. The obtained polymer solution was analyzed by GPC and LC to find that Mw=6,090, Mw/Mn=1.44, and remaining low molecular weight components with Mw of less than 200=0.00% (LC area %).

[Example 22] Production of 4-HS/TBMA Copolymer

A grass vessel was fed with 589 g of a 25 mass % 4-HS/MEK solution (the chromatogram area of 4-HS was 99.8% in GPC analysis when the total chromatogram area of components other than MEK was considered as 100), 267 g of TBMA, 55 g of dimethyl 2,2'-azobis(2-methylpropionate), and 84 g of MEK, followed by dissolution to prepare a solution to be added dropwise.

Another 2 L-grass vessel was fed with 325 g of MEK and heated to 79° C. with stirring. To this, the solution to be added dropwise was added dropwise for 4 hours, allowed to continue the reaction for additional 2 hours, and then cooled to room temperature. To the polymer solution was added a mixed solution containing 2 mass % methanol in hexane to precipitate a polymer, and stirred, followed by decantation to isolate the polymer. The polymer was redissolved in a mixed solution containing 7 mass % methanol in acetone, to which hexane was added to precipitate a polymer and stirred, followed by decantation to isolate the polymer, which operations were repeated four times.

The polymer was redissolved in acetone, to which PGMEA was added, followed by distillation under reduced pressure to finally obtain 1580 g of a solution containing 20 mass % polymer in PGMEA. $^{13}$C-NMR analysis resulted in finding that the composition ratio of the obtained copolymer was 4-HS/TBMA=38.8/61.2.

[Example 23] Production of 4-HS/ECpMA Copolymer

To a vessel were added 83.6 g of 25 mass % 4-HS/PGMEA solution obtained in Example 3 (the chromatogram area of 4-HS was 99.9% in GPC analysis when the total chromatogram area of components other than PGMEA was considered as 100), 46.2 g of ECpMA, 11.4 g of 2,2-azobisisobutyric acid dimethyl, and 15.4 g of PGMEA, and mixed to prepare a monomer solution.

A glass 500-mL four-necked flask reactor equipped with a stirrer, condenser, and thermometer was fed with 67.1 g of PGMEA, allowed to have nitrogen atmosphere, and then heated to 79° C. To the reactor, the monomer solution was fed dropwise for 4 hours at a constant rate, and then the reaction was continued for additional 2 hours. The temperature during the polymerization reaction was controlled within 79.0 to 80.5° C., and then cooled to room temperature after the completion of polymerization.

Then, 200 g of the polymer solution was mixed with 460 g of n-hexane and 20 g of methanol with stirring to precipitate a polymer, and then left to stand, followed by decantation to isolate the polymer. The polymer was redissolved in a mixed solution of 40 g of acetone and 20 g of methanol, to which 400 g of n-hexane was added with stirring to precipitate a polymer, followed by decantation to isolate the polymer, which operations were repeated four times.

The collected polymer was dissolved in 80 g of acetone. A part of the polymer solution was sampled, and dried under reduced pressure at 40° C. to obtain powder of the polymer, which was then subjected to NMR analysis. The monomer composition ratio (molar ratio) of the polymer by the NMR analysis was 4-HS:ECpMA=42.6:57.4.

The remaining polymer solution was distilled with acetone evaporated off at a heat source temperature of 45° C. under reduced pressure and with addition of PGMEA to replace the solvent with PGMEA, thereby finally obtaining a solution of 4-HS/ECpMA copolymer with a polymer concentration of 20 mass % in PGMEA. The obtained polymer solution was analyzed by GPC and LC to find that Mw=5810, Mw/Mn=1.47, and remaining low molecular weight components with Mw of less than 200=0.01% (LC area %).

INDUSTRIAL AVAILABILITY

The 4-hydroxystyrene solution of the present invention with high purity and good storage stability can be used as a material of resist polymers for EUV lithography and electron beam lithography. Furthermore, the solution can be used to produce a 4-hydroxystyrene polymer suitable as a resist for EUV lithography and electron beam lithography by a simple process without the need for deprotection step and on a commercial scale.

The invention claimed is:

1. A method of producing a 4-hydroxystyrene solution, comprising the following steps (i) to (iv):

(i) deprotection step for contacting 4-acetoxystyrene with a base in a solvent at −20° C. to 20° C. to produce 4-hydroxystyrene;

(ii) neutralization step for adding an acid to the solution containing 4-hydroxystyrene after deprotection to neutralize the solution;

(iii) step for washing the solution containing 4-hydroxystyrene after neutralization with water;

(iv) solvent replacement step for adding a solvent that can dissolve 4-hydroxystyrene to the solution containing 4-hydroxystyrene followed by distillation at 40° C. or lower to remove other components than 4-hydroxystyrene and excess solvent.

2. The method of producing a 4-hydroxystyrene solution according to claim 1, wherein the base used in the deprotection step is subjected to bubbling with an inert gas to remove dissolved oxygen before use, and wherein the deprotection step is performed under a nitrogen atmosphere.

3. The method of producing a 4-hydroxystyrene solution according to claim 1, wherein the acid used in the neutralization step is subjected to bubbling with an inert gas to remove dissolved oxygen before use.

4. The method of producing a 4-hydroxystyrene solution according to claim 1, wherein the base used in the deprotection step is a base selected from the group consisting of lithium hydroxide, sodium hydroxide, potassium hydroxide, sodium methoxide, potassium methoxide, sodium ethoxide, potassium tert-butoxide, trimethylamine, triethylamine, ethanolamine, diazabicycloundecene, diazabicyclononene, 1,5,7-triazabicyclo[4.4.0]dec-5-ene, 7-methyl-1,5,7-triazabicyclo[4.4.0]dec-5-ene, 1,1,3,3-tetramethylguanidine, and tetramethylammonium hydroxide.

5. The method of producing a 4-hydroxystyrene solution according to claim 1, wherein the organic solvent used in the solvent replacement step is any one organic solvent selected from the group consisting of alcohols, ketones, ethers, glycol ethers, glycol ether esters, and esters.

6. The method of producing a 4-hydroxystyrene solution according to claim 1, wherein the final concentration of 4-hydroxystyrene in the solvent replacement step is 10 to 70 mass %.

7. The method of producing a 4-hydroxystyrene solution according to claim 1, further comprising a step of allowing the 4-hydroxystyrene solution to pass through a filter with nominal pore size of 1 μm or less before and/or after the solvent replacement step.

8. A 4-hydroxystyrene solution, in which the concentration of 4-hydroxystyrene is from 10 to 70 mass %, and the chromatogram area of 4-hydroxystyrene in a gel permeation chromatography analysis of the solution is 99.5% or more when the total chromatogram area of components other than the organic solvent is considered as 100.

9. The 4-hydroxystyrene solution according to claim 8, wherein the chromatogram area of 4-hydroxystyrene polymer relative to the chromatogram area of 4-hydroxystyrene in a gel permeation chromatography analysis of the solution is 0.5% or less.

10. The 4-hydroxystyrene solution according to claim 8, wherein the chromatogram area of 4-hydroxystyrene is 99.7% or more.

11. The 4-hydroxystyrene solution according to claim 8, wherein the chromatogram area of 4-hydroxystyrene is 99.9% or more.

12. The 4-hydroxystyrene solution according to claim 8, wherein the organic solvent is any one organic solvent selected from the group consisting of alcohols, ketones, ethers, glycol ethers, glycol ether esters, and esters.

13. The 4-hydroxystyrene solution according to claim 8, which does not comprise a polymerization inhibitor.

14. A polymerization material of resist polymers, comprising the 4-hydroxystyrene solution according to claim 8.

15. A method of producing a polymer having a structural unit derived from 4-hydroxystyrene, comprising polymerization using the 4-hydroxystyrene solution according to claim 8 as a polymerization material alone or in combination with anther monomer that can be copolymerized with the polymerization material.

16. A method of producing a polymer having a structural unit derived from 4-hydroxystyrene, comprising polymerization of the 4-hydroxystyrene solution produced by the method according to claim 1 as a polymerization material alone or in combination with anther monomer that can be copolymerized with the polymerization material.

17. A method of producing a polymer having a structural unit derived from 4-hydroxystyrene, comprising:

a step of producing a 4-hydroxystyrene solution by the method according to claim 1; and a step of polymerization using the 4-hydroxystyrene solution produced in the above step as a polymerization material alone or in combination with another monomer that can be copolymerized with 4-hydroxystyrene.

18. A method of producing a polymer according to claim 15, wherein the another copolymerizable monomer include a monomer having an acid dissociable group.

19. A method of producing a polymer according to claim 18, wherein the monomer having an acid dissociable group is a group having a tertiary carbon atom bound to an oxygen atom.

20. A method of producing a polymer according to claim 15, wherein the method is applied in polymerization using a polymerization tank with a volume of 30 L or more.

* * * * *